(12) United States Patent
Kim et al.

(10) Patent No.: US 12,181,409 B2
(45) Date of Patent: *Dec. 31, 2024

(54) CELL IMAGING COMPOSITION AND CELLULAR MATERIAL IMAGING METHOD USING SAME

(71) Applicants: EWHA UNIVERSITY-INDUSTRY COLLABORATION FOUNDATION, Seoul (KR); KYTECBIO CO., LTD., Seoul (KR)

(72) Inventors: Kwan Mook Kim, Seoul (KR); Juyoung Yoon, Seoul (KR); Sun Shin Cha, Seoul (KR); Ah-Young Song, Seoul (KR)

(73) Assignees: EWHA UNIVERSITY-INDUSTRY COLLABORATION FOUNDATION, Seoul (KR); KYTECBIO CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/741,512

(22) Filed: May 11, 2022

(65) Prior Publication Data

US 2022/0267670 A1 Aug. 25, 2022

Related U.S. Application Data

(63) Continuation of application No. PCT/KR2020/015922, filed on Nov. 12, 2020.

(30) Foreign Application Priority Data

Nov. 12, 2019 (KR) ........................ 10-2019-0144581

(51) Int. Cl.
*G01N 33/50* (2006.01)
*C07F 5/02* (2006.01)
(Continued)

(52) U.S. Cl.
CPC ......... *G01N 21/6428* (2013.01); *C07F 5/025* (2013.01); *G01N 21/77* (2013.01);
(Continued)

(58) Field of Classification Search
CPC ............... G01N 21/6428; G01N 21/77; G01N 33/5005; G01N 2021/6439;
(Continued)

(56) References Cited

U.S. PATENT DOCUMENTS

| 11,780,857 | B2* | 10/2023 | Kim ........................ C07F 5/025 |
| | | | 436/111 |
| 2014/0161729 | A1* | 6/2014 | Barany ................ C07D 401/06 |
| | | | 544/137 |
| 2020/0347080 | A1* | 11/2020 | Kim .......................... C07F 5/02 |

FOREIGN PATENT DOCUMENTS

| CN | 103118710 A | 5/2013 |
| CN | 110055054 A | 7/2019 |

(Continued)

OTHER PUBLICATIONS

Song, Ah-young. A borane sensor for amino alcohol to determine enantionmeric excess and concentration via circular dichroism and fluorescence [Master's thesis, Ewha Womans University]. <https://dspace.ewha.ac.kr/handle/2015.oak/249073> (Feb. 18, 2019) (Year: 2019).*

(Continued)

*Primary Examiner* — Jennifer Wecker
*Assistant Examiner* — Michelle Adams
(74) *Attorney, Agent, or Firm* — Shih IP Law Group, PLLC.

(57) ABSTRACT

The present disclosure relates to a composition for cell imaging including a probe compound, and a method of cell-material imaging using the same. The composition for cell imaging and the method of cell-material imaging are (Continued)

provided to image the material in the cell by measuring fluorescence generated by reacting the probe and a material in a cell.

16 Claims, 45 Drawing Sheets

(51) Int. Cl.
*G01N 21/64* (2006.01)
*G01N 21/77* (2006.01)

(52) U.S. Cl.
CPC .............. *G01N 33/5005* (2013.01); *G01N 2021/6439* (2013.01); *G01N 2021/7786* (2013.01); *Y10T 436/173845* (2015.01)

(58) Field of Classification Search
CPC ............ G01N 2021/7786; C07F 5/025; Y10T 436/173845
See application file for complete search history.

(56) References Cited

FOREIGN PATENT DOCUMENTS

| CN | 110894201 A | 3/2020 |
|---|---|---|
| KR | 10-2014-0098436 A | 8/2014 |
| KR | 10-2020-0122259 A | 10/2020 |

OTHER PUBLICATIONS

Reja, R.M et al. "Lysine-Targeting Reversible Covalent Inhibitors with Long Residence Time," J. Am. Chem. Soc. 2022, 144, 1152-1157 (Year: 2022).*

International Search Report of PCT/KR2020/015922 dated Feb. 19, 2021.

Rui Zhang et al., Mono- and di-phenylboronic acid receptors with fluorescence sensitivity to d-fructose, Sensors and Actuators B: Chemical. 2014, vol. 198, pp. 260-267.

Xiaolong Sun et al., The mechanisms of boronate ester formation and fluorescent turn-on in ortho aminomethylphenylboronic acids, Nature Chemistry, vol. 11, Sep. 2019, pp. 768-778.

Marcus D. Phillips et al., Boronic Acid Based Modular Fluorescent Sensors for Glucose, Journal of Fluorescence. 2004, vol. 14, Sep. 2004, pp. 549-559.

Mukesh Eknath Shirbhate et al., Optical and Fluorescent Dual Sensing of Aminoalcohols by in Situ Generation of BODIPY-like Chromophore, Journal of the American Chemical Society 2020, vol. 142, pp. 4975-4979.

Richard Wombacher et al., Chemical tags: applications in live cell fluorescence imaging, Journal of Biophotonics, vol. 4, No. 6, pp. 391-402 (2011).

Ellen M. Sletten et al., Bioorthogonal Chemistry: Fishing for Selectivity in a Sea of Functionality, Angewandte Chemie. 2009, vol. 48, pp. 6974-6998.

Richard D. Carpenter et al., Copper-Free Click for PET: Rapid 1,3-Dipolar Cycloadditions with a Fluorine-18 Cyclooctyne, ACS Medicinal Chemistry Letter 2011, vol. 2, pp. 885-889.

Hartmuth C. Kolb et al., Click Chemistry: Diverse Chemical Function from a Few Good Reactions, Angewandte Chemie. 2001, vol. 40, pp. 2004-2021.

Xinghai Ning et al., Visualizing Metabolically Labeled Glycoconjugates of Living Cells by Copper-Free and Fast Huisgen Cycloadditions, Angewandte Chemie. 2008, vol. 47, pp. 2253-2255.

Wenjiao Song et al., A Photoinducible 1,3-Dipolar Cycloaddition Reaction for Rapid, Selective Modification of Tetrazole-Containing Proteins, Angewandte Chemie. 2008, vol. 47, pp. 2832-2835.

European Search Report of EP application No. 20887834.8 dated on Oct. 25, 2023.

Adrian S. Culf et al., A spectroscopic study of substituted anthranilic acids as sensitive environmental probes for detecting cancer cells, Bioorganic & Medicinal Chemistry, vol. 24, pp. 929-937. (2016).

* cited by examiner

FIG. 6E(ii)

FIG. 6E(iii)
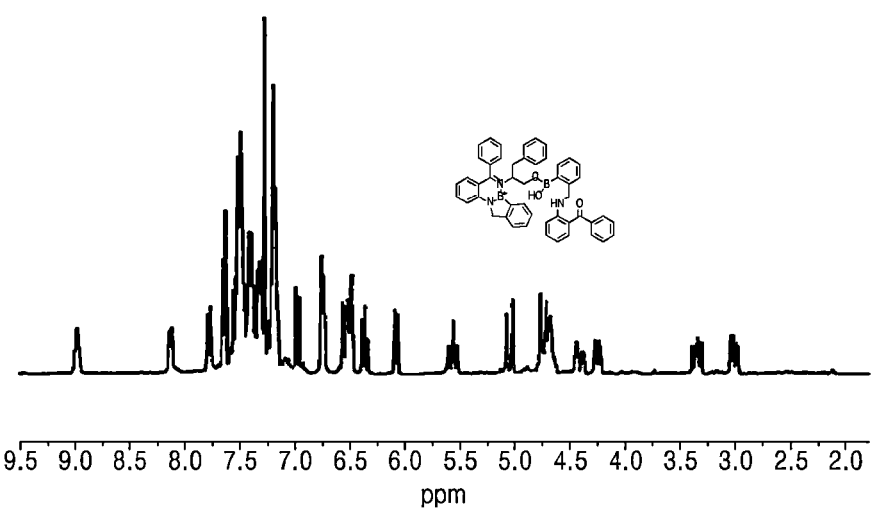
FIG. 6E(iv)
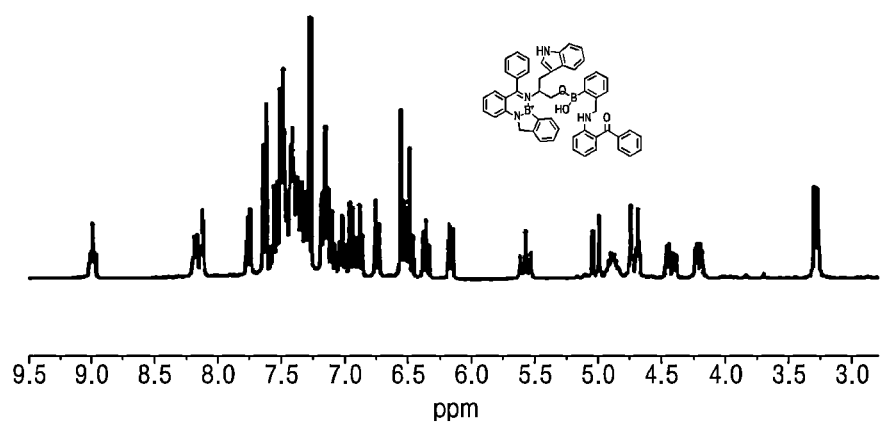

FIG. 12A(iii)
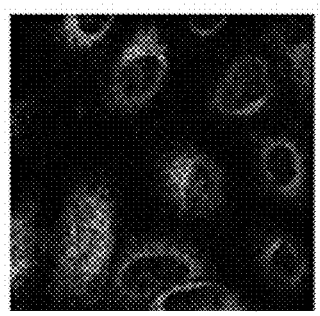
FIG. 12A(iv)
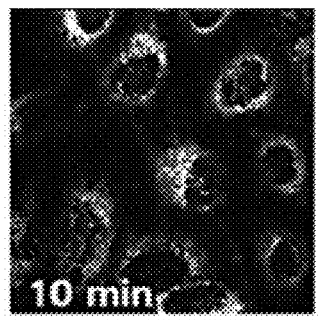

*FIG. 12A(vi)*

FIG. 12A(vii)
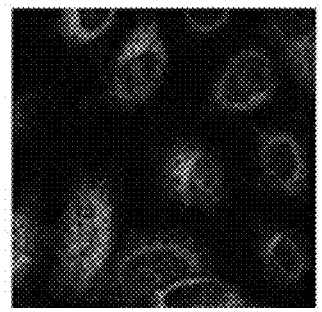
FIG. 12A(viii)
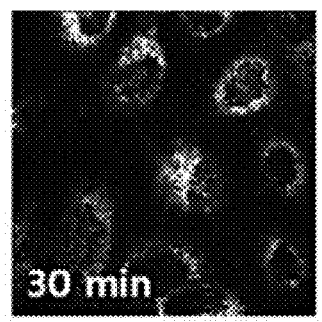

pH 7.4, 0.5 h
BSA, HSA, Avidin, Insulin

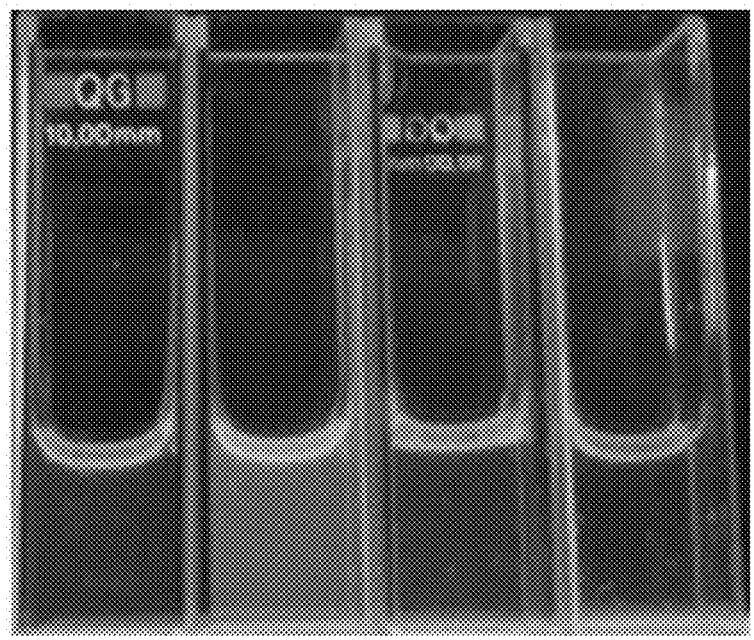
*FIG. 14D(ii)*
pH 7.4, 1.5 h
BSA, HSA, Avidin, Insulin

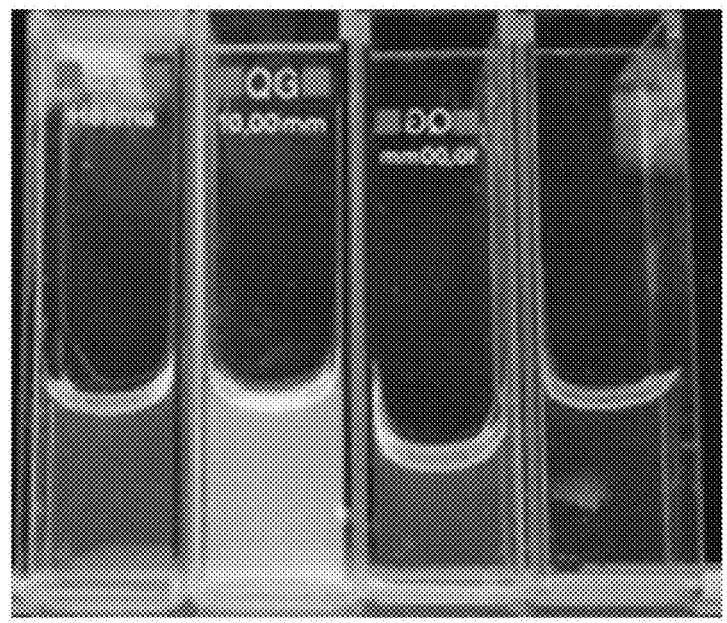
FIG. 14D(iii)
pH 8.5, 0.5 h
BSA, HSA, Avidin, Insulin

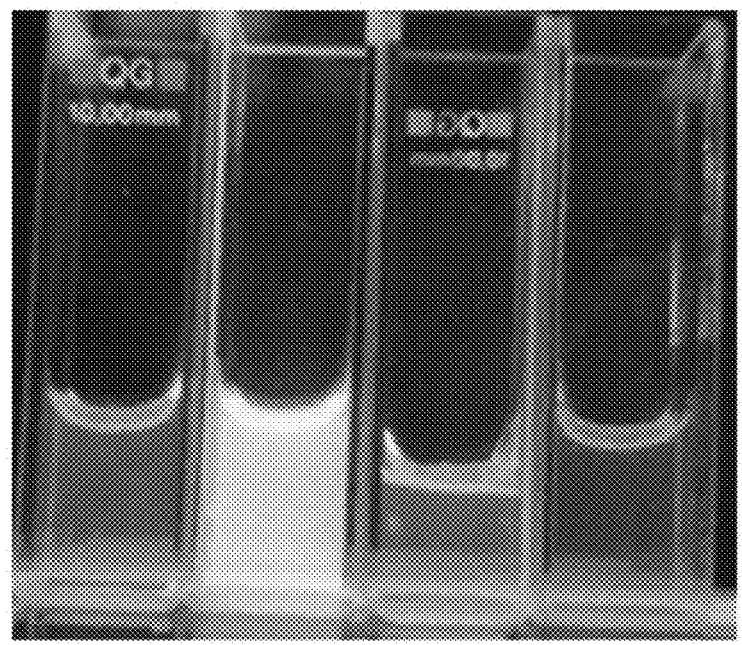
FIG. 14D(iv)
pH 8.5, 1.5 h
BSA, HSA, Avidin, Insulin

CurA, 0.5 h
pH 7.4 0eq, 2eq
pH 8.5 0eq, 2eq

FIG. 14D(vi)
CurA, 1.5 h
pH 7.4 0eq, 2eq
pH 8.5 0eq, 2eq
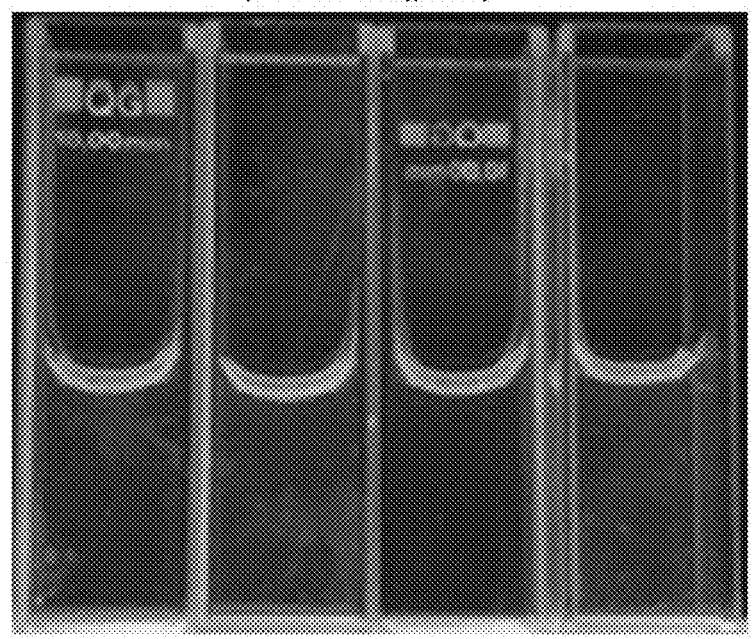

CELL IMAGING COMPOSITION AND CELLULAR MATERIAL IMAGING METHOD USING SAME

CROSS-REFERENCE TO RELATED APPLICATIONS

This application is a continuation of PCT Application No. PCT/KR2020/015922, filed on Nov. 12, 2020, which claims priority to Korean Patent Application Number 10-2019-0144581, filed on Nov. 12, 2019, all of which are hereby incorporated by reference in their entirety.

TECHNICAL FIELD

The present disclosure relates to a composition for cell imaging including a fluorescent probe compound and a method of cell-material imaging using the same.

BACKGROUND

The present inventors developed a new compound that selectively reacts with aminoalcohol to form a structure similar to Bodipy and thus exhibits strong circular dichroism (CD) and fluorescence.

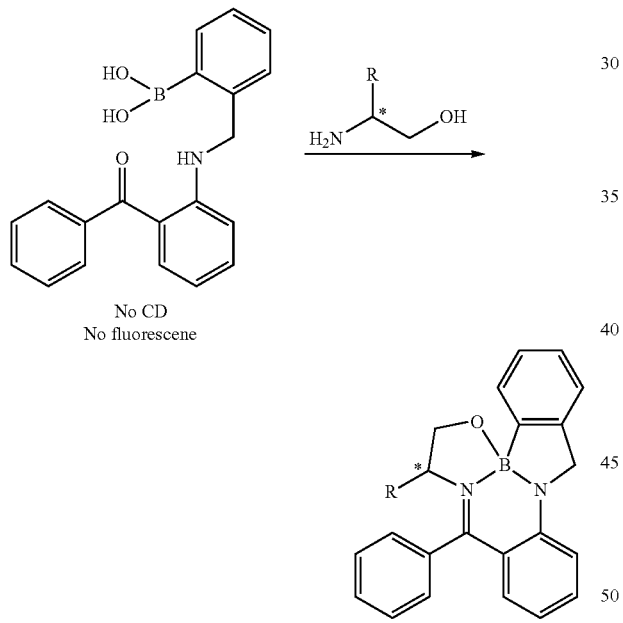

The above reaction scheme shows the new compound (Compound 1) that reacts with aminoalcohol and exhibits strong CD as shown in FIG. 16 and fluorescence as shown in FIG. 18. The scheme of delocalized It (bottom) and π* (top) orbitals of the new compound (Compound 1) is shown in FIG. 17.

In cells, which are considered the basic units of life, organelles such as mitochondria, endoplasmic reticulum and reticulum; and biomolecules such as lipids, amino acid derivatives and proteins exist. Fluorescent imaging of their intracellular locations in real time plays a big role in diagnosing related diseases and aging and researching treatment and prevention in addition to clarifying their functions. Currently, in order to image a specific protein, the protein bonded to a green fluorescent protein (GFP) by genetic manipulation is expressed or an antibody with a fluorescent chromophore attached thereto is injected. Using a fluorescent protein makes it difficult to control the fluorescence intensity and color, requires significant time and cost as well as high-level technology. Also, since the fluorescent protein cannot pass through the cell membrane, it is necessary to squeeze the cell and then dissolve the cell membrane. For this reason, there is a need for a small molecular weight synthetic compound that can be bonded to a protein and can produce fluorescence. Such compounds can substitute for antibodies and thus can be widely used in research on protein functions as well as diagnosis and treatment of diseases targeting proteins.

Although many chemical-tags that induce fluorescence in proteins have been developed so far, such a chemical tag requires complex manipulations to introduce an adapter, such as a peptide, to a target protein and modify the structure thereof (J. Biophotonics 4, No. 6, 391-402 (2011)).

Recently, bioorthogonal conjugation techniques have been developed that use a relatively simple organic compound to generate fluorescence specific to a protein or specific biomolecule in a living body. The term "bioorthogonal conjugation" was first used by Carolyn R. Bertozzi, and generally requires two steps of manipulation (Sletten, Ellen M., Bertozzi, Carolyn R., "Bioorthogonal Chemistry: Fishing for Selectivity in a Sea of Functionality" Angewandte Chemie International Edition. 2009, 48(38), 6974-6998). Copper-free click chemistry is known as a representative bioorthogonal conjugation. This enables a strain-promoted alkyne-azide cycloaddition reaction by primarily binding azide ($-N_3$ compound) to a target protein or lipid and then adding a probe to which cyclooctyne is attached (Carpenter, Richard D., Hausner, Sven H., Sutcliffe, Julie L., "Copper-Free Click for PET: Rapid 1,3-Dipolar Cycloadditions with a Fluorine-18 Cyclooctyne", ACS Medicinal Chemistry Letters. 2011, 2 (12): 885-889)). In addition to this, various bioorthogonal conjugation techniques have been developed (Kolb, Hartmuth C., Finn, M. G., Sharpless, K. Barry, Angewandte Chemie, International Edition (2001), 40(11), 2004-2021; Ning, X. H., Guo, J., Wolfert, M. A., and Boons, G.-J. Angew. Chem., Int. Ed. 2008, 47, 2253; Song, W., Wang, Y., Qu, J., Madden, M. M., and Lin, Q. Angew. Chem., Int. Ed. 2008, 47, 2832).

DISCLOSURE OF THE INVENTION

Problems to be Solved by the Invention

The present disclosure relates to a composition for cell imaging including a fluorescent probe compound and a method of cell-material imaging using the same.

However, problems to be solved by the present disclosure are not limited to the above-described problems. Although not described herein, other problems to be solved by the present disclosure can be clearly understood by those skilled in the art from the following descriptions.

Means for Solving the Problems

A first aspect of the present disclosure provides a composition for cell imaging, including a fluorescent probe compound, represented by the following Chemical Formula 1:

[Chemical Formula 1]

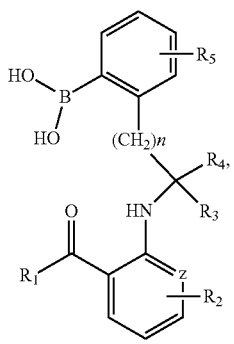

in the above Chemical Formula 1,
each of $R_1$, $R_2$, $R_3$, $R_4$ and $R_5$ is independently selected from the group consisting of hydrogen, a halogen group, amino group, nitro group, cyano group, formyl group, carboxyl group, a $C_{1-10}$ alkyl group, a $C_{1-10}$ alkylcarbonyl group, a $C_{6-10}$ aryl group and a $C_{1-10}$ alkoxy group,
when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, hydroxy group, amino group, cyano group, nitro group and a $C_{6-10}$ aryl group,
Z is —N—, —O— or —CH, and
n is an integer of from 0 to 5.

A second aspect of the present disclosure provides a method of cell-material imaging, including measuring fluorescence generated by reacting a fluorescent probe compound, represented by the following Chemical Formula 1, and a material in a target cell:

[Chemical Formula 1]

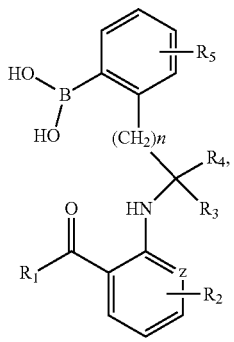

In the above Chemical Formula 1,
each of $R_1$, $R_2$, $R_3$, $R_4$ and $R_5$ is independently selected from the group consisting of hydrogen, a halogen group, amino group, nitro group, cyano group, formyl group, carboxyl group, a $C_{1-10}$ alkyl group, a $C_{1-10}$ alkylcarbonyl group, a $C_{6-10}$ aryl group and a $C_{1-10}$ alkoxy group,
when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, hydroxy group, amino group, cyano group, nitro group and a $C_{6-10}$ aryl group,
Z is —N—, —O— or —CH, and
n is an integer of from 0 to 5.

Effects of the Invention

According to embodiments of the present disclosure, the composition for cell imaging and the method of cell-material imaging can be used to obtain a fluorescent image of a material in a living cell, for example, a cell-material or organelle of a living cell.

According to embodiments of the present disclosure, the composition for cell imaging and the method of cell-material imaging are provided to image the material in the cell by measuring fluorescence generated by reacting the probe and a material in a cell, and the composition for cell imaging and the method of cell-material imaging can be used for fluorescent imaging of material in a cell including mitochondria, DNA, golgi body, reticulum, lysosome, protein, $Hg^{2+}$, $Cu^{2+}$, ATP, amino acid or ROS (reactive oxygen species).

According to embodiments of the present disclosure, the composition for cell imaging and the method of cell-material imaging can be used for fluorescent imaging of stem cells, endoplasmic reticulum or cancer cells.

According to embodiments of the present disclosure, the composition for cell imaging and the method of cell-material imaging can be used for fluorescent imaging of stem cells, endoplasmic reticulum or cancer cells by imaging mitochondria and/or proteins in cells. Therefore, the composition for cell imaging and the method of cell-material imaging can be used for diagnosis and/or treatment of diseases (particularly, neoplastic disease or cancer).

According to the embodiments of the present disclosure, the composition for cell imaging and the method of cell-material imaging can selectively sense various proteins depending on environmental conditions such as pH. For example, the composition for cell imaging and the method of cell-material imaging have a superior selectivity to human serum albumin (HSA) among various proteins and thus can selectively sense a cell containing HSA.

BEST MODE FOR CARRYING OUT THE INVENTION

Figure 1A:
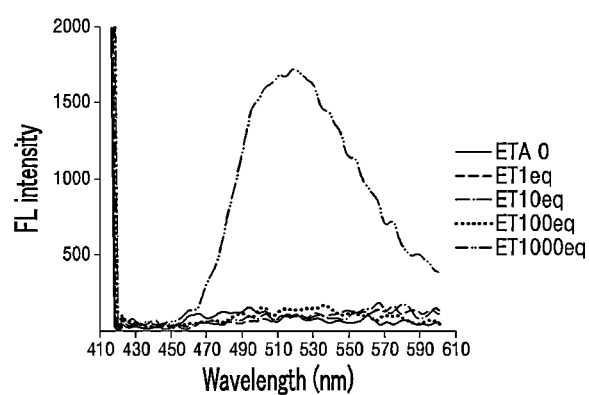
FIGS. 1A to 1H show fluorescence spectra trend for Compound 1+ethanolamine (FIG. 1A), Compound 1+alaninol (FIG. 1B), Compound 1+phenylalaninol (FIG. 1C), Compound 1+aminobutanol (FIG. 1D), Compound 1+valinol (FIG. 1E), Compound 1+leucinol (FIG. 1F), Compound 1+tryptophanol (FIG. 1G), and comparison (Compound 1+alaninol, leucinol, aminobutanol, phenylalaninol) (may be omitted) (FIG. 1H), respectively, when used Compound 1 as a probe, according to an example of the present disclosure.
Figure 1B:
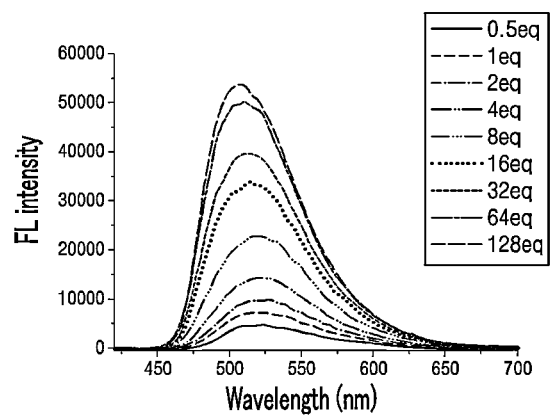
Figure 1C:
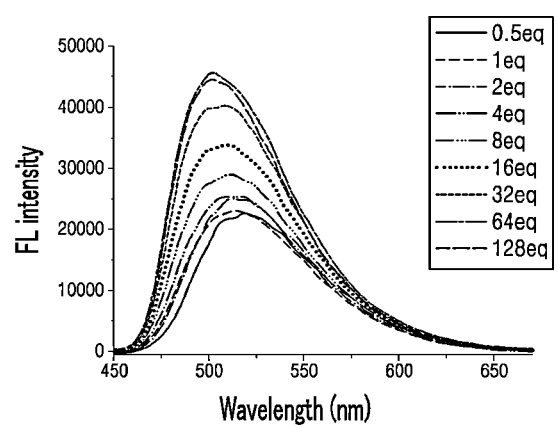
Figure 1D:
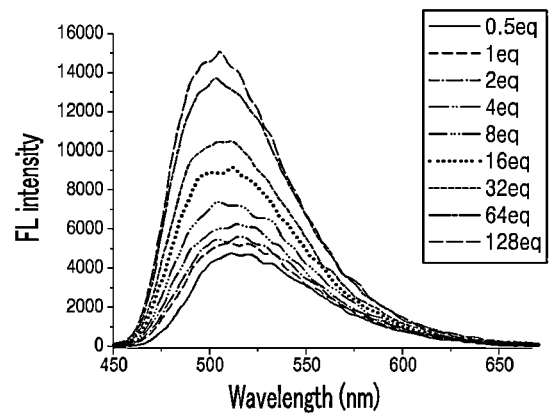
Figure 1E:
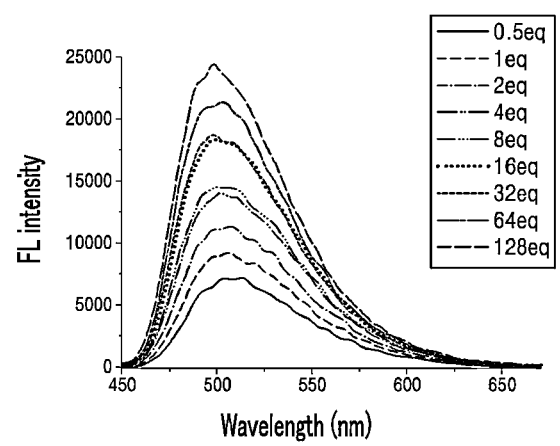
Figure 1F:
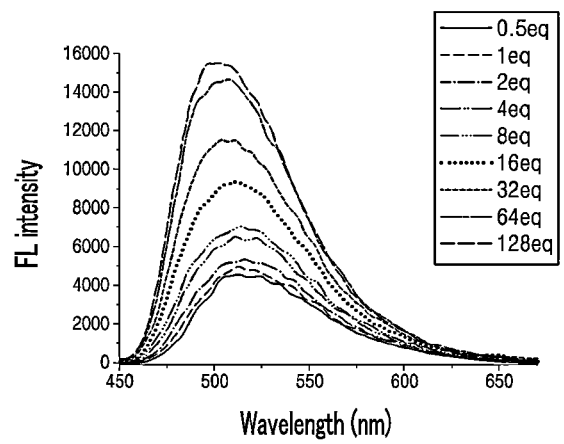
Figure 1G:
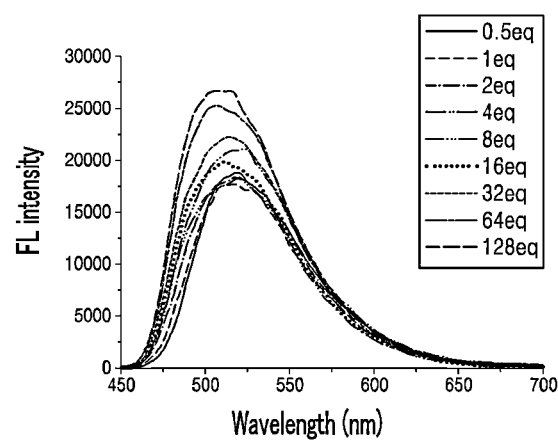
Figure 1H:
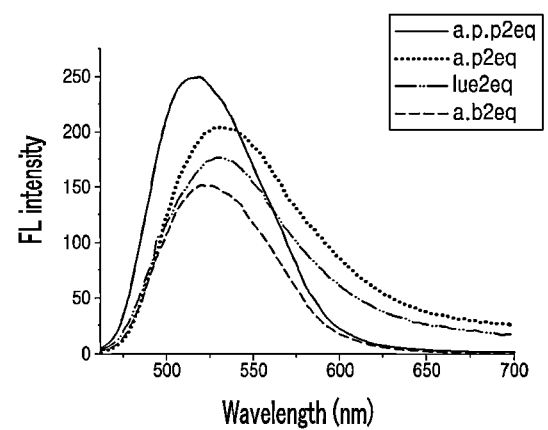

Hereinafter, embodiments and examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl (group)" includes a linear or branched saturated or unsaturated $C_{1-20}$ alkyl group, and may include, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicodecyl, or all the possible isomers thereof, but may not be limited thereto.

Through the whole document, the term "alkenyl (group)" refers to a monovalent hydrocarbon group including at least one carbon-carbon double bond in an alkyl (group) having two or more carbon atoms among the above-described alkyl (groups), and may include a linear or branched $C_{2-20}$ alkenyl (group), but may not be limited thereto.

Through the whole document, the term "alkynyl (group)" refers to a monovalent hydrocarbon group including at least one carbon-carbon double bond in an alkyl (group) having two or more carbon atoms among the above-described alkyl (groups), and may include a linear or branched $C_{2-20}$ alkynyl (group), but may not be limited thereto.

Through the whole document, the term "aryl (group)" refers to a monovalent functional group formed by the removal of one hydrogen atom from one or more rings of arene, and may include, for example, phenyl, biphenyl, terphenyl, naphthyl, anthryl, phenanthryl, pyrenyl, or all the possible isomers thereof, but may not be limited thereto. The arene may refer to a hydrocarbon group having an aromatic ring, and includes monocyclic and polycyclic hydrocarbon groups. The polycyclic hydrocarbon group includes one or more aromatic rings and includes an aromatic or non-aromatic ring as an additional ring, but may not be limited thereto.

Through the whole document, the term "cycloalkyl (group)" refers to a monovalent functional group having a saturated hydrocarbon ring, and may include a $C_{3-8}$ cycloalkyl (group), for example, cyclopropyl, cylcobutyl, cyclopentyl, cyclohexyl, cycloheptyl, cyclooctyl or all the possible isomers thereof, but may not be limited thereto.

Through the whole document, the term "alkoxy" refers to the above-defined alkyl groups connected to an oxygen atom, and may include a $C_{1-20}$ alkoxy (group), for example, methoxy, ethoxy, propoxy, butoxy, pentoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, acosanyloxy or all the possible isomers thereof, but may not be limited thereto.

Through the whole document, the term "halo group" refers to a halogen element from Group 17 of the periodic table included as a functional group in a compound, and the halogen element may include, for example, F, Cl, Br or I, but may not be limited thereto.

Hereinafter, embodiments and examples of the present disclosure will be described in detail with reference to the accompanying drawings. However, the present disclosure may not be limited to the following embodiments, examples, and drawings.

A first aspect of the present disclosure provides a composition for cell imaging, including a fluorescent probe compound, represented by the following Chemical Formula 1:

[Chemical Formula 1]

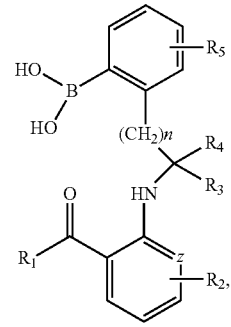

in the above Chemical Formula 1, each of $R_1$, $R_2$, $R_3$, $R_4$ and $R_5$ is independently selected from the group consisting of hydrogen, a halogen group, amino group, nitro group, cyano group, formyl group, carboxyl group, a $C_{1-10}$ alkyl group, a $C_{1-10}$ alkylcarbonyl group, a $C_{6-10}$ aryl group and a $C_{1-10}$ alkoxy group, when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, hydroxy group, amino group, cyano group, nitro group and a $C_{6-10}$ aryl group, Z is —N—, —O— or —CH, and n is an integer of from 0 to 5.

In an embodiment of the present disclosure, the fluorescent probe compound may include at least one of the following compound:

[Compound 1]

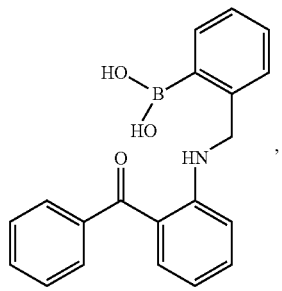

[Compound 2]

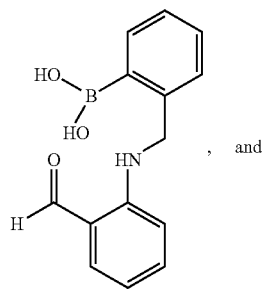

, and

[Compound 3]

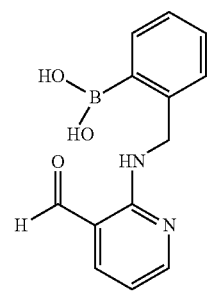

In an embodiment of the present disclosure, the composition for cell imaging is used to image a material in a living cell, but is not limited thereto.

In an embodiment of the present disclosure, the composition for cell imaging is provided to image the material in the cell by measuring fluorescence generated by reacting the probe and a material in a cell, but may not be limited thereto.

In an embodiment of the present disclosure, the material in the cell includes a cell-material or an organelle, but may not be limited thereto.

In an embodiment of the present disclosure, the material in the cell includes cytoplasm, mitochondria, proteins or biomolecules, but may not be limited thereto.

In an embodiment of the present disclosure, the material in the cell includes mitochondria, DNA, golgi body, reticulum, lysosome, protein, $Hg^{2+}$, $Cu^{2+}$, ATP, amino acid or ROS (reactive oxygen species), but may not be limited thereto.

In an embodiment of the present disclosure, the organelle includes mitochondria and/or proteins so that stem cells, endoplasmic reticulum or cancer cells are imaged, but may not be limited thereto.

In an embodiment of the present disclosure, the composition for cell imaging and the method of cell-material imaging can be used for fluorescent imaging of stem cells, endoplasmic reticulum or cancer cells by imaging mitochondria and/or proteins in cells. Therefore, the composition for cell imaging and the method of cell-material imaging can be used for diagnosis and/or treatment of diseases (particularly, neoplastic disease or cancer). According to an embodiment of the present disclosure, the composition for cell imaging and the method of cell-material imaging can selectively sense various proteins depending on environmental conditions such as pH. When the composition for cell imaging and the method of cell-material imaging are applied, the types of protein that can be sensed depending on the experiment and/or incubation environment can be expanded, and, thus, the composition for cell imaging and the method of cell-material imaging are not particularly limited to the types of protein.

In an embodiment of the present disclosure, the compound of Chemical Formula 1 exhibits an excellent effect on fluorescent imaging of HSA among the proteins, and exhibits superior fluorescence intensity and selectivity for HSA. Therefore, the compound of Chemical Formula 1 can selectively sense a cell containing HSA.

In an embodiment of the present disclosure, an appropriate pH range for selective fluorescent imaging of the HSA with the composition for cell imaging may be from about pH 7 to about pH 11, but may not be limited thereto. For example, the pH range may be from about pH 7 to about pH 11, from about pH 7 to about pH 10, from about pH 7 to about pH 9, from about pH 7 to about pH 8.5, from about pH 7.5 to about pH 11, from about pH 7.5 to about pH 10, from about pH 7.5 to about pH 9, or from about pH 7.5 to about pH 8.5, but may not be limited thereto. In an embodiment of the present disclosure, an appropriate pH range for selective fluorescent imaging of the HSA with the composition for cell imaging may be from about pH 7.5 to about pH 8.5.

In an embodiment of the present disclosure, in a method of fluorescent imaging of the cell-material or organelle, the mechanism by which the fluorescent probe compound performs fluorescent imaging of the mitochondria is presumed to be due to a fluorescent chromophore produced by reaction with phosphatidyl-ethanolamine present in the mitochondrial membrane.

In an embodiment of the present disclosure, when a cell is treated with the composition for cell imaging, the composition for cell imaging generates a specific fluorescence in a mitochondrial organelle. Therefore, the composition for cell imaging can be used as a probe for determining the shape and activity of mitochondria.

In an embodiment of the present disclosure, the material in the cell includes a biomaterial selected from the group consisting of amino acid, nucleotide, amino acid ester, amino acid amide and combinations thereof containing an amine compound including aminoalcohol, but may not be limited thereto.

In an embodiment of the present disclosure, the probe compound forms an imine bond with an amino group contained in the amine compound included in the intracellular material. Boron (B) contained in the probe compound connects a nitrogen (N) atom contained in the probe compound and a nitrogen (N) atom contained in the amine compound to form a fluorescent chromophore including an N—B—N bond-containing hetero ring in-situ. The fluorescent chromophore may be used to individually or simultaneously analyze fluorescence and circular dichroism (CD). However, the present disclosure may not be limited thereto.

In an embodiment of the present disclosure, the Compound 1 may be synthesized using a method known in the art. For example, the Compound 1 may be synthesized by the method of the following Reaction Scheme 1, but may not be limited thereto:

In an embodiment of the present disclosure, the amine compound may include at least one of the following compounds, but may not be limited thereto:

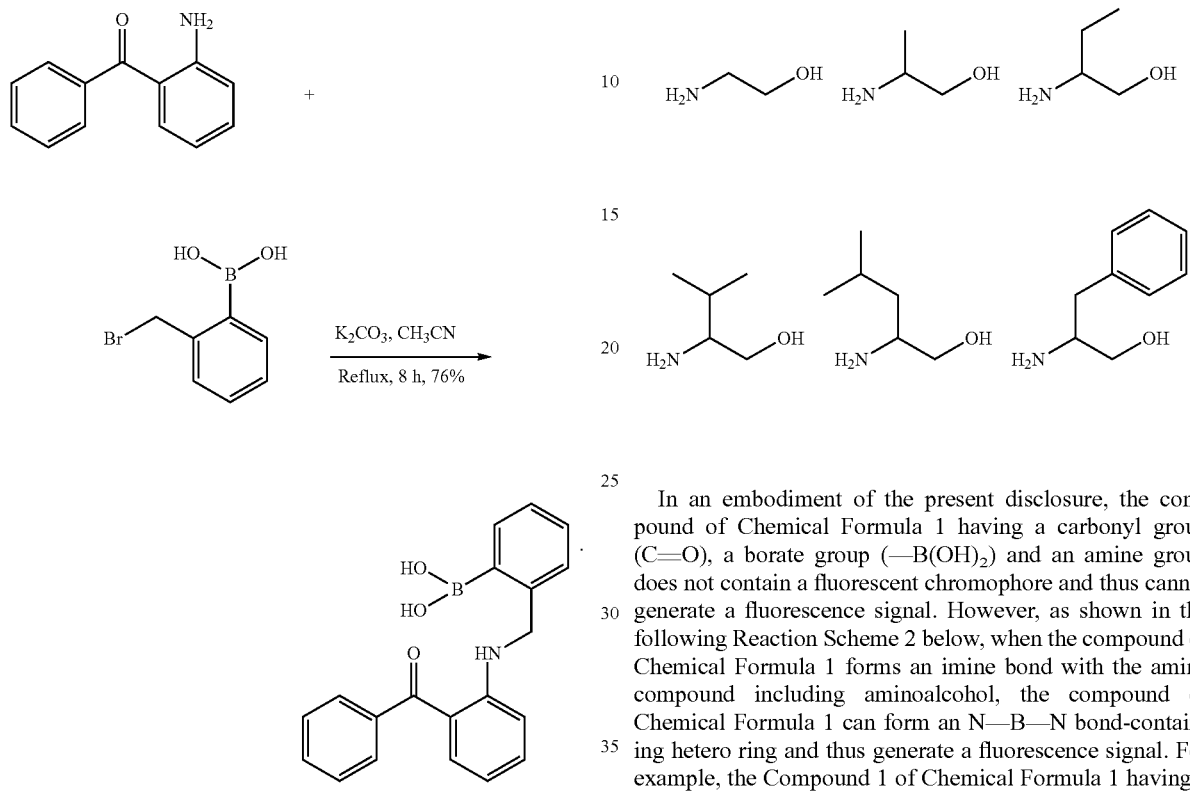

[Reaction Scheme 1]

In an embodiment of the present disclosure, the amine compound including aminoalcohol includes an amine compound represented by the following Chemical Formula 2, but may not be limited thereto:

[Chemical Formula 2]

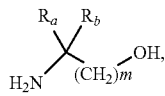

in the above Chemical Formula 2, each of $R_a$ and $R_b$ is independently selected from the group consisting of hydrogen, a halogen group, amino group, nitro group, cyano group, formyl group, carboxyl group, a $C_{1-10}$ alkyl group, a $C_{1-10}$ alkylcarbonyl group, a $C_{6-10}$ aryl group and a $C_{1-10}$ alkoxy group, when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, hydroxy group, amino group, cyano group, nitro group and a $C_{6-10}$ aryl group, and m is an integer of from 0 to 5.

In an embodiment of the present disclosure, the compound of Chemical Formula 1 having a carbonyl group (C=O), a borate group (—B(OH)$_2$) and an amine group does not contain a fluorescent chromophore and thus cannot generate a fluorescence signal. However, as shown in the following Reaction Scheme 2 below, when the compound of Chemical Formula 1 forms an imine bond with the amine compound including aminoalcohol, the compound of Chemical Formula 1 can form an N—B—N bond-containing hetero ring and thus generate a fluorescence signal. For example, the Compound 1 of Chemical Formula 1 having a carbonyl group (C=O), a borate group (—B(OH)$_2$) and an amine group does not contain a fluorescent chromophore and thus cannot generate a fluorescence signal. However, as shown in the following Reaction Scheme 2 below, when the Compound 1 forms an imine bond with the amine compound including aminoalcohol, the Compound 1 can form an N—B—N bond-containing hetero ring and thus generate a fluorescence signal (FIGS. 1A to 1H).

[Reaction Scheme 2]

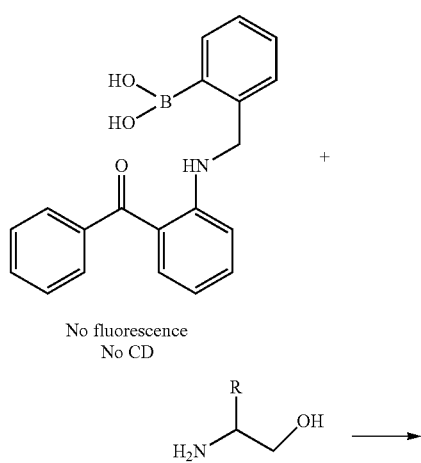

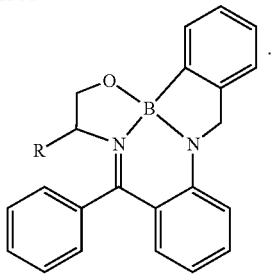

Strong fluorescence
Strong CD

That is, the Compound 1 forms an imine bond with aminoalcohol as shown in the Reaction Scheme 2 and boron connects N and N to form a fluorescent chromophore including an N—B—N bond-containing hetero ring, and, thus, the Compound 1 can generate a fluorescence signal. The generation of fluorescence from aminoalcohol in this way is novel and has not been reported before. That is, the fluorescent probe compound represented by the Chemical Formula 1 has a carbonyl group (C=O) as a functional group that can react with various amine groups to form imine and also has a boric acid group (—B(OH)$_2$) for forming the imine.

In an embodiment of the present disclosure, a carbonyl group (C=O) and a boric acid group (—B(OH)$_2$) in the compound of Chemical Formula 1 and aminoalcohol form an adduct having an N—B—N bond-containing hetero ring as shown in the Reaction Scheme 2, which can be predicted from HRMS data, $^{11}$B NMR data, $^1$H NMR data and $^{13}$C NMR data obtained from the reaction between the compound of Chemical Formula 1, such as the Compound 1 and ethanol amine (FIGS. 2A and 2B, FIGS. 3A and 3B, and FIGS. 4A and 4B).

Meanwhile, the following Comparative Compound 1 and the following Comparative Compound 2, which are similar to the Compound 1 but do not have a boric acid group (—B(OH)$_2$), have a carbonyl group (C=O) but cannot react to form imine with aminoalcohol under normal room temperature conditions (FIGS. 5A to 5D), and thus cannot generate a fluorescence signal or a CD signal. An uryl group of the Comparative Compound 2 has properties as a Lewis acid like a boric acid but cannot react with aminoalcohol. Therefore, it can be seen that the boric acid of the Compound 1 plays a special role in forming imine and an N—B—N hetero ring.

Comparative Compound 2

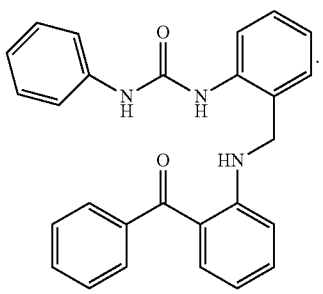

Also, the following Comparative Compound 3 has a fluorescent chromophore of a naphthylamine group, but fluorescence is quenched by an unshared electron pair present in N under normal conditions, and even in the presence of aminoalcohol, the Comparative Compound 3 cannot make a significant change in fluorescence or CD. Therefore, it can be seen that the generation of fluorescence or CD by the Compound 1 in the presence of aminoalcohol is closely related to the formation of an N—B—N hetero ring.

Comparative Compound 3

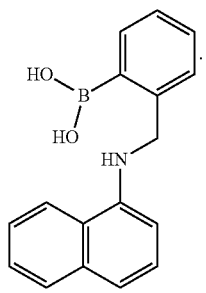

Comparative Compound 1

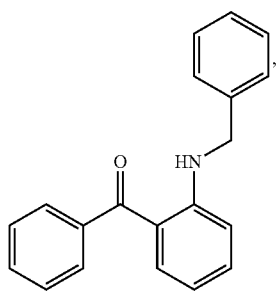

In an embodiment of the present disclosure, the Compound 1 does not form imine with amine that does not have an additional functional group, such as —OH or —NH, which can be bonded to boron. For example, the Compound 1 does not react with methylamine, ethylamine, phenylethylamine and the like under normal room temperature conditions. As a result, the Compound 1 can distinguish an amine compound that has an additional functional group, such as —OH or —NH, from an amine compound that does not have an additional functional group (Reaction Scheme 3).

[Reaction Scheme 3]
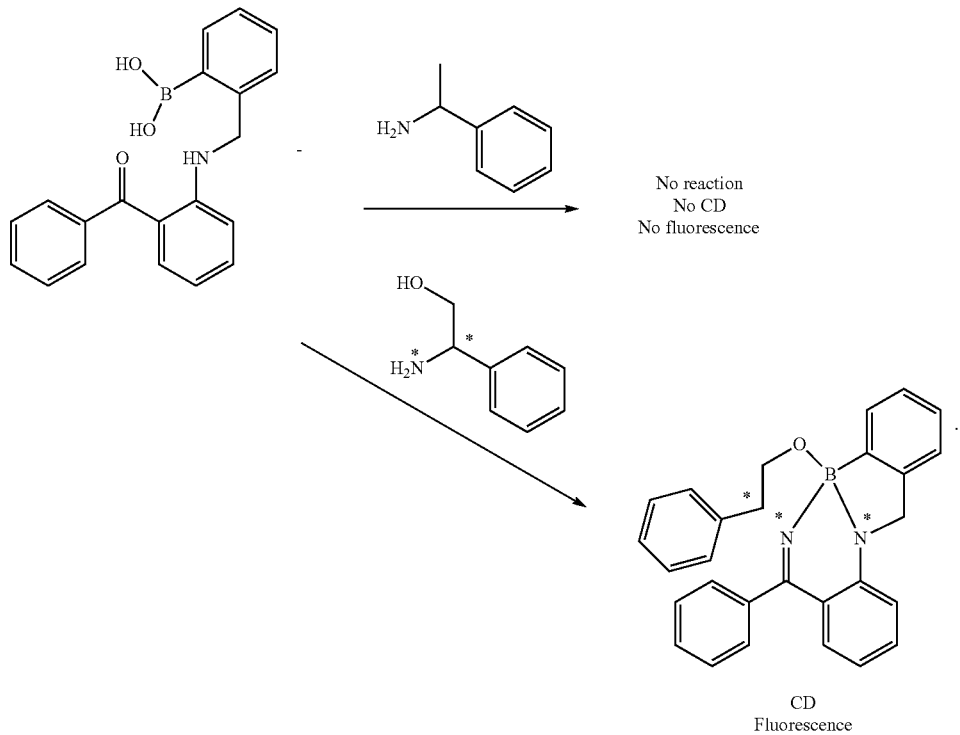
In an example of the present disclosure, fluorescence is somewhat different for each kind of amine compound including aminoalcohol. This shows that if the Compound 1 is used as a probe compound, it is possible to identify even the type of a substrate (Reaction Scheme 4).
[Reaction Scheme 4]
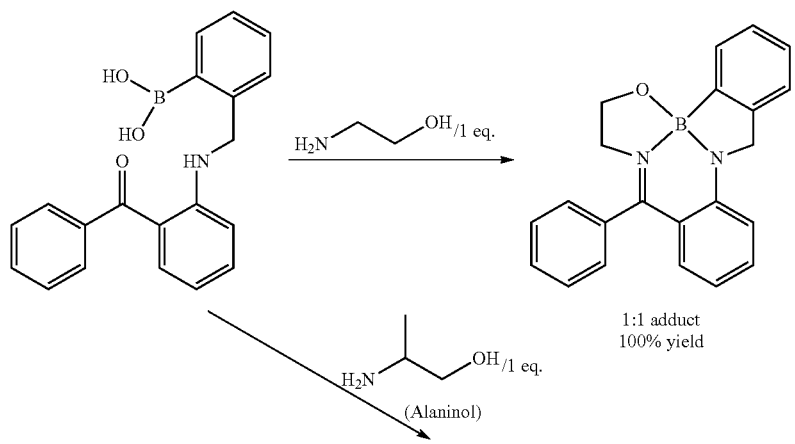

-continued

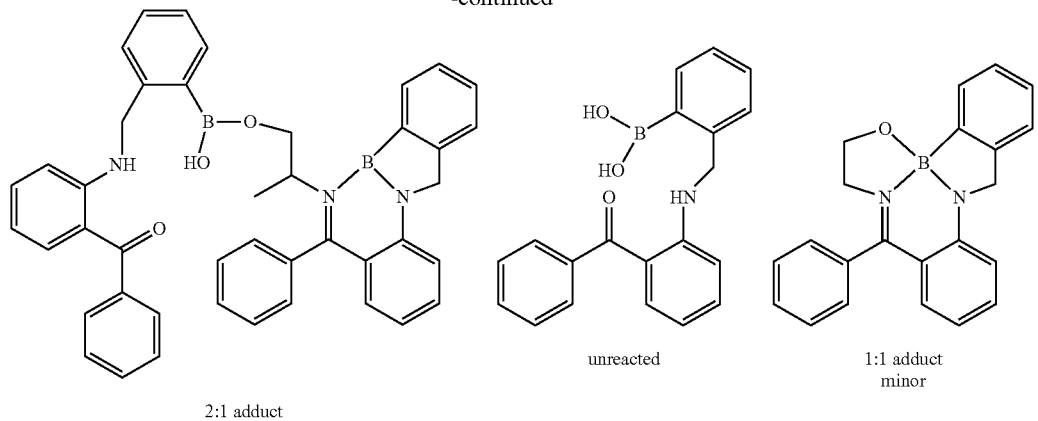

2:1 adduct
unreacted
1:1 adduct minor

In an embodiment of the present disclosure, the compound of the Chemical Formula 1 does not contain a fluorescent chromophore, but reacts with an amine compound including aminoalcohol to form a fluorescent chromophore. As a result, there is a great difference in the intensity of fluorescence between in the presence and absence of aminoalcohol within the amine compound. Therefore, this result shows that the compound of Chemical Formula 1 is very useful as a fluorescence sensor.

In an embodiment of the present disclosure, a substrate that can generate a fluorescence signal by reacting with the probe compound includes aminoalcohol represented by the Chemical Formula 2 above and means a biomaterial selected from the group consisting of amino acid, nucleotide, amino acid ester, amino acid amide and combinations thereof.

A second aspect of the present disclosure provides a method of cell-material imaging, including measuring fluorescence generated by reacting a fluorescent probe compound, represented by the following Chemical Formula 1, and a material in a target cell:

[Chemical Formula 1]

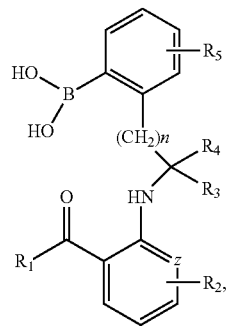

In the above Chemical Formula 1,
each of $R_1$, $R_2$, $R_3$, $R_4$ and $R_5$ is independently selected from the group consisting of hydrogen, a halogen group, amino group, nitro group, cyano group, formyl group, carboxyl group, a $C_{1-10}$ alkyl group, a $C_{1-10}$ alkylcarbonyl group, a $C_{6-10}$ aryl group and a $C_{1-10}$ alkoxy group,
when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, hydroxy group, amino group, cyano group, nitro group and a $C_{6-10}$ aryl group,
Z is —N—, —O— or —CH, and
n is an integer of from 0 to 5.

Detailed descriptions on the second aspect of the present disclosure, which overlap with those on the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, the target cell is a living cell, but is not limited thereto.

In an embodiment of the present disclosure, the method of cell-material imaging further includes obtaining an image of the material in the target cell by measuring fluorescence generated by reacting the probe compound and the material in the target cell, but is not limited thereto.

In an embodiment of the present disclosure, the material in the target cell includes a cell-material or an organelle, but is not limited thereto.

In an embodiment of the present disclosure, the material in the target cell includes cytoplasm, mitochondria, proteins or biomolecules, but is not limited thereto.

In an embodiment of the present disclosure, the material in the target cell includes mitochondria, DNA, golgi body, reticulum, lysosome, protein, $Hg^{2+}$, $Cu^{2+}$, ATP, amino acid or ROS (reactive oxygen species), but is not limited thereto.

In an embodiment of the present disclosure, the organelle includes mitochondria and/or proteins so that stem cells, endoplasmic reticulum or cancer cells are imaged, but is not limited thereto.

In an embodiment of the present disclosure, the composition for cell imaging and the method of cell-material imaging can be used for fluorescent imaging of stem cells, endoplasmic reticulum or cancer cells by imaging mitochondria and/or proteins in cells. Therefore, the cell imaging composition and the cell-material imaging method can be used for diagnosis and/or treatment of diseases (particularly, neoplastic disease or cancer). According to an embodiment of the present disclosure, the composition for cell imaging and the method of cell-material imaging can selectively sense various proteins depending on environmental conditions such as pH. When the composition for cell imaging and the method of cell-material imaging are applied, the types of protein that can be sensed depending on the experiment and/or incubation environment can be expanded, and, thus, the composition for cell imaging and the method of cell-material imaging are not particularly limited to the types of protein.

In an embodiment of the present disclosure, the compound of Chemical Formula 1 exhibits an excellent effect on fluorescent imaging of HSA among the proteins, and exhibits superior fluorescence intensity and selectivity for HSA. Therefore, the compound of Chemical Formula 1 can selectively sense a cell containing HSA.

In an embodiment of the present disclosure, an appropriate pH range for selective fluorescent imaging of the HSA with the composition for cell imaging may be from about pH 7 to about pH 11, but may not be limited thereto. For example, the pH range may be from about pH 7 to about pH 11, from about pH 7 to about pH 10, from about pH 7 to about pH 9, from about pH 7 to about pH 8.5, from about pH 7.5 to about pH 11, from about pH 7.5 to about pH 10, from about pH 7.5 to about pH 9, or from about pH 7.5 to about pH 8.5, but may not be limited thereto. In an embodiment of the present disclosure, an appropriate pH range for selective fluorescent imaging of the HSA with the composition for cell imaging may be from about pH 7.5 to about pH 8.5.

In an embodiment of the present disclosure, in a method of fluorescent imaging of the cell-material or organelle, the mechanism by which the fluorescent probe compound performs fluorescent imaging of the mitochondria is presumed to be due to a fluorescent chromophore produced by reaction with phosphatidyl-ethanolamine present in the mitochondrial membrane.

In an embodiment of the present disclosure, when a cell is treated with the composition of Chemical formula 1, the composition of Chemical formula 1 generates a specific fluorescence in a mitochondrial organelle. Therefore, the composition of Chemical formula 1 can be used as a probe for determining the shape and activity of mitochondria.

In an embodiment of the present disclosure, the material in the target cell includes a biomaterial selected from the group consisting of amino acid, nucleotide, amino acid ester, amino acid amide and combinations thereof containing an amine compound including aminoalcohol, but may not be limited thereto.

In an embodiment of the present disclosure, the probe compound forms an imine bond with an amino group contained in the amine compound included in the intracellular material. Boron (B) contained in the probe compound connects a nitrogen (N) atom contained in the probe compound and a nitrogen (N) atom contained in the amine compound to form a fluorescent chromophore including an N—B—N bond-containing hetero ring in-situ. The fluorescent chromophore may be used to individually or simultaneously analyze fluorescence and circular dichroism (CD). However, the present disclosure may not be limited thereto.

Hereinafter, example embodiments are described in more detail by using Examples, but the present disclosure may not limited to the Examples.

Mode for Carrying Out the Invention

EXAMPLES

Example 1: Synthesis of Compound 1

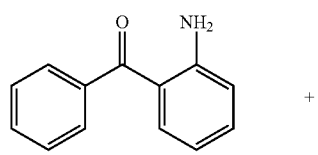

2-aminobenzophenone (2.00 g, 10.1 mmol), 2-bromomethylphenyl boronic acid (2.59 g, 12.1 mmol) and potassium carbonate (1.39 g, 10.1 mmol) were added into an acetonitrile solvent (15 mL) and refluxed for 8 hours. Immediately after the reaction solution was dried using an evaporator, Compound 1 (2.5 g, 7.6 mmol) was obtained by silica gel column chromatography using EA/hexane (¼) as a developer.

Yield: 76%. $^1$H NMR (300 MHz, CD$_3$CN): δ 7.64-7.61; (m, 1H), 7.60-7.59; (m, 1H), 7.58-7.55; (m, 2H), 7.53-7.52; (m, 1H), 7.51-7.47; (m, 1H), 7.43-7.39; (m, 2H), 7.38-7.33; (m, 2H), 7.30-7.25; (m, 1H), 6.88; (d, 1H, 9 Hz), 6.59-6.54; (m, 1H), 4.65; (s, 2H). $^{13}$C NMR (125 MHz, CDCl$_3$): 199.58, 151.38, 143.75, 140.62, 135.42, 135.20, 134.56, 131.24, 129.91, 129.11, 128.39, 128.01, 126.77, 114.63, 112.68, 46.99. HRMS (EI): calcd for C$_{20}$H$_{19}$N$_1$O$_1$B$_1$[M+H]$^+$: 332.1850; found: 332.2168.

Example 2: Measurement of Fluorescence Spectrum of Mixture of Compound 1 and Aminoalcohol Instrument: Scinco FS-2
Concentration of Compound 1: 1.5 mM
Result: FIGS. 1A to 1H Referring to the fluorescence spectrum in FIGS. 1A to 1H, changes in the fluorescence spectrum when Compound 1 is used as a probe can be seen: Compound 1+ethanolamine (1A), Compound 1+alaninol (1B), Compound 1+phenylalaninol (1C), Compound 1+aminobutanol (1D), Compound 1+valinol (1E), Compound 1+leucinol (1F), Compound 1+tryptophanol (1G), and comparison (Compound 1+alaninol, leucinol, aminobutanol, phenylalaninol) (may be omitted) (1H).

Figure 2A:
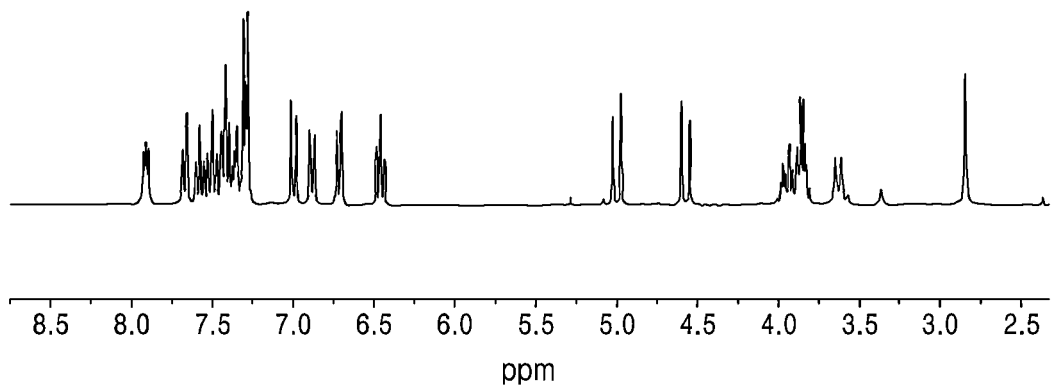
FIGS. 2A and 2B show $^1H$ NMR spectra of 1:1 adduct formation by reaction of Compound 1 and ethanolamine (FIG. 2A), and Compound 1 (FIG. 2B), respectively, according to an example of the present disclosure.

Example 3: Reaction Between Compound 1 and Other Amines and Measurement of Fluorescence Spectrum The instrument, concentration and parameters were the same as those for ethanolamine and alaninol.
Result: FIGS. 1A to 1H Example 4: Comparison of reactivity of Compound 1 and Aminoalcohol After Compound 1 (30 mg) was dissolved in 1 mL of CDCl$_3$, 0.5 eq, 1 eq, 2 eq, 5 eq and 10 eq of aminoalcohol were sequentially added and stirred for 30 minutes each time. As a result, ¹H NMR spectra were obtained (FIG. 2A). The aminoalcohol used in the experiment is as follows:

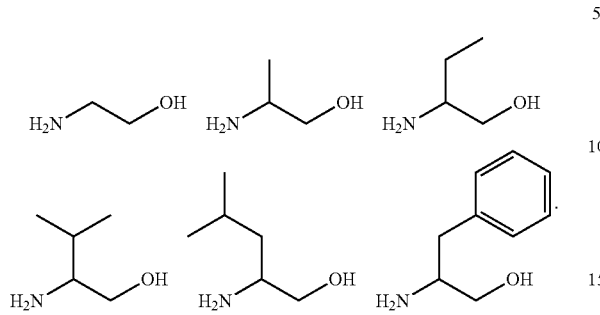

No reaction occurred even when up to 10 eq of aminopropanol was added to vials in which the Comparative Compounds 1, 2 and 3 as comparative examples were dissolved, respectively. CD and fluorescence were measured for the mixture of each of Comparative Compounds 1, 2 and 3 and aminopropanol, but no change occurred.

Figure 2B:
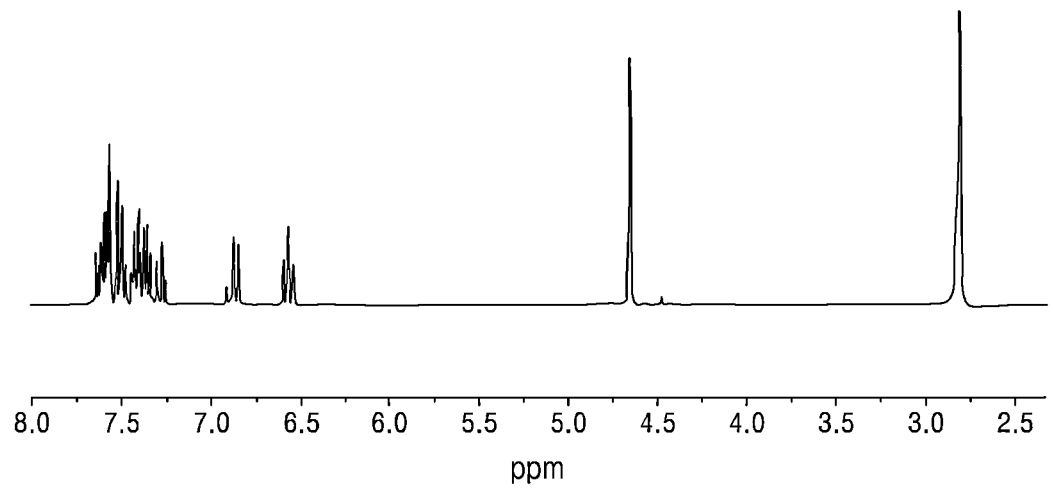

Referring to FIGS. 2A and 2B, ¹H NMR spectrum of 1:1 adduct formation by reaction of Compound 1 and ethanolamine (2A), and ¹H NMR spectrum of Compound 1 (2B) can be seen.

Figure 3A:
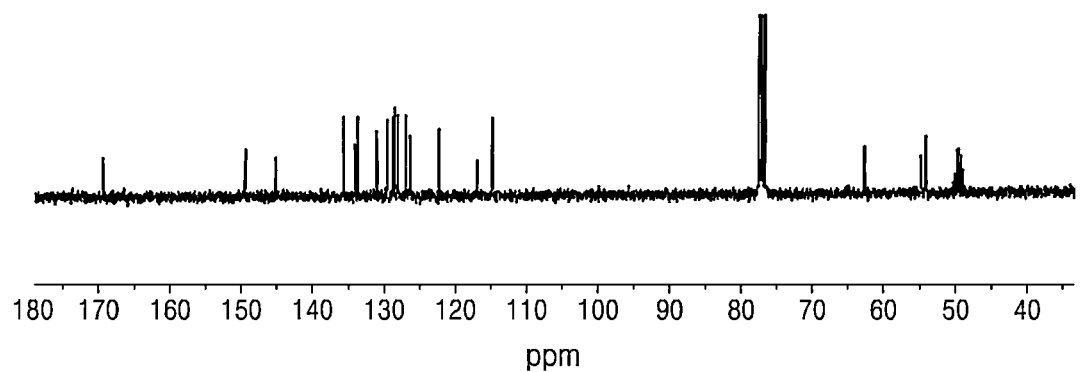
FIGS. 3A and 3B show $^{13}C$ NMR spectra of 1:1 adduct formation by reaction of Compound 1 and ethanolamine (FIG. 3A), and Compound 1 (FIG. 3B), respectively, according to an example of the present disclosure.
Figure 3B:
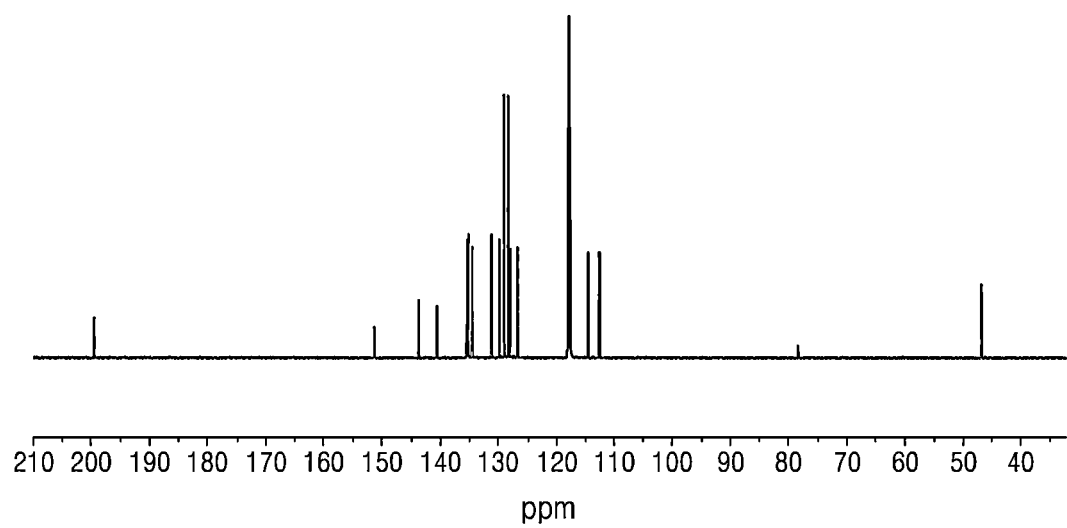

Referring to FIGS. 3A and 3B, ¹³C NMR spectrum of 1:1 adduct formation by reaction of Compound 1 and ethanolamine (3A), and ¹³C NMR spectrum of Compound 1 (3B) can be seen.

Figure 4A:
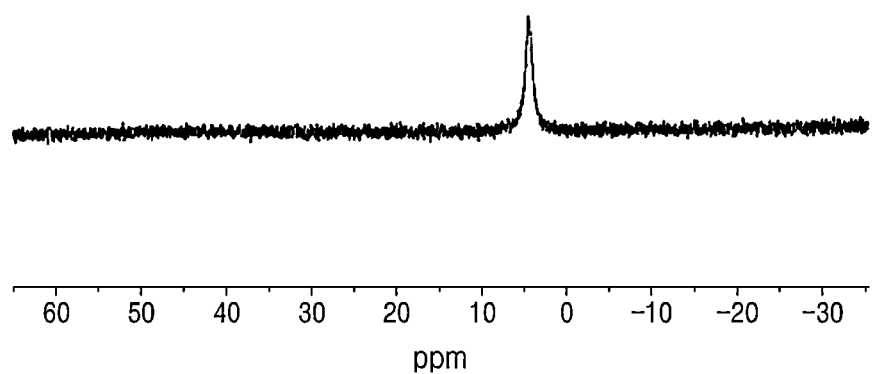
FIGS. 4A and 4B show $^{11}B$ NMR spectra of 1:1 adduct formation by reaction of Compound 1 and ethanolamine (FIG. 4A), and Compound 1 (FIG. 4B), respectively, according to an example of the present disclosure.
Figure 4B:
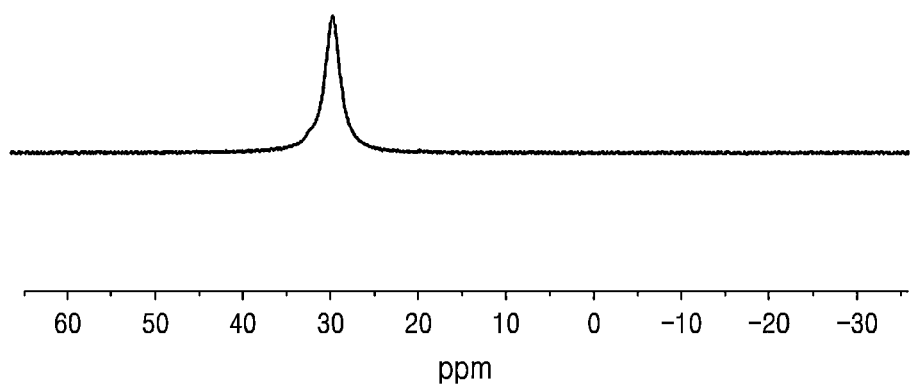
Figure 5A:
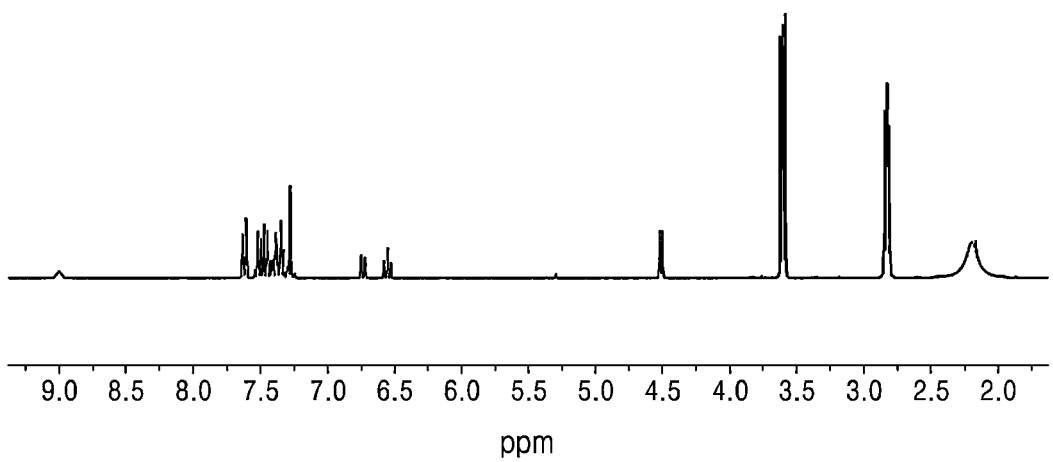
FIGS. 5A to 5D show $^1H$ NMR spectra of 1:5 adduct formation by reaction of Comparative Compound 1 and ethanolamine (FIG. 5A), Comparative Compound 1 (FIG. 5B), 1:5 adduct formation by reaction of Comparative Compound 2 and ethanolamine (FIG. 5C), and Comparative Compound 2 (FIG. 5D), respectively, according to an comparative example of the present disclosure.
Figure 5B:
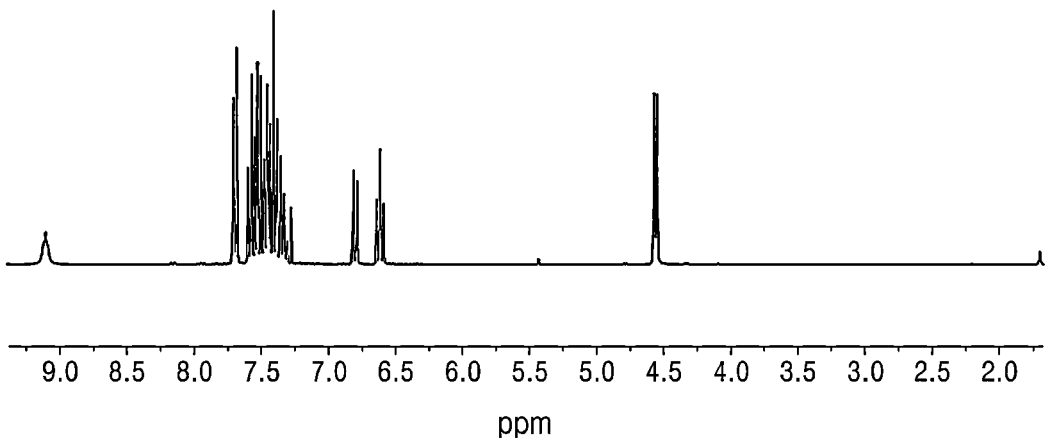
Figure 5C:
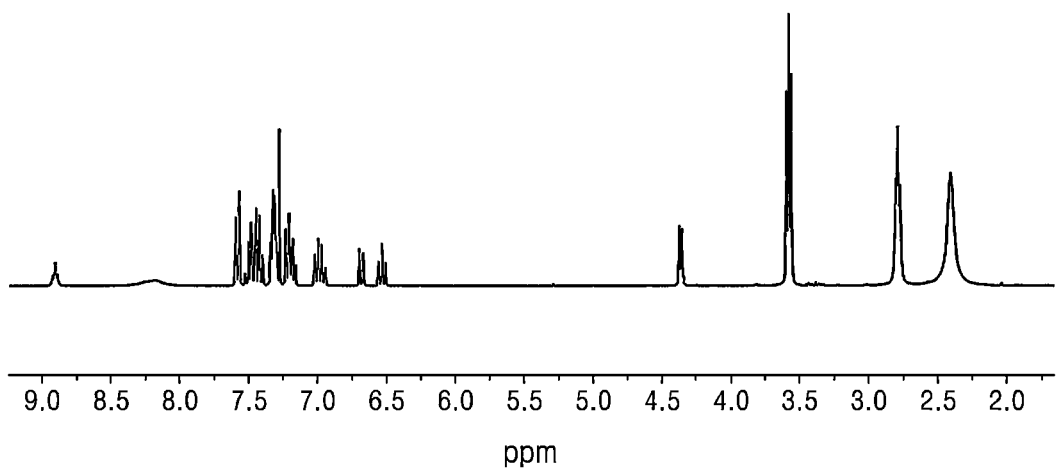
Figure 5D:
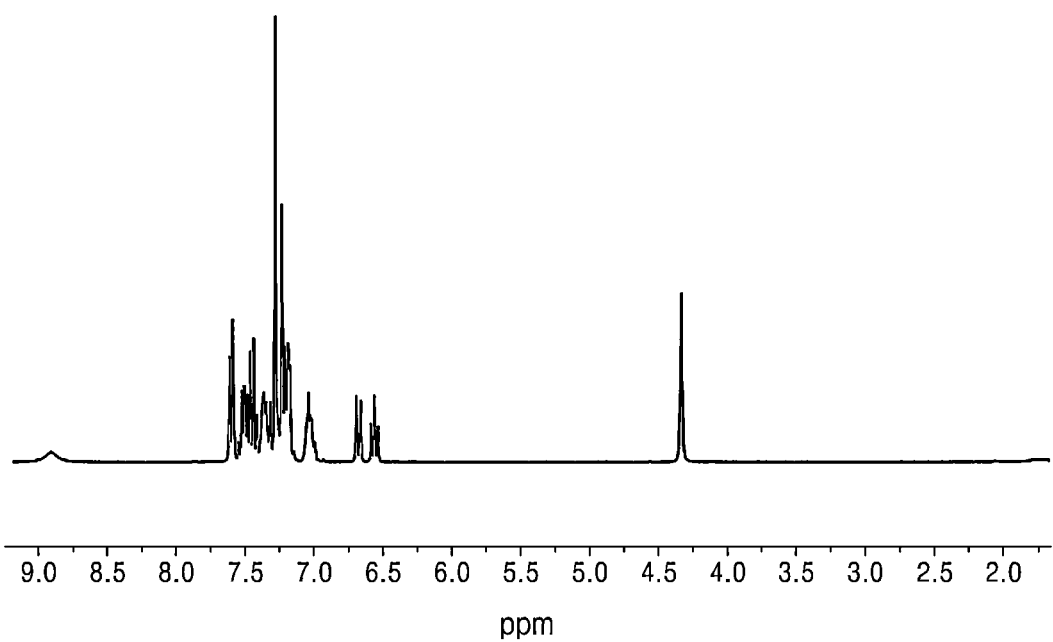
Figure 6A:
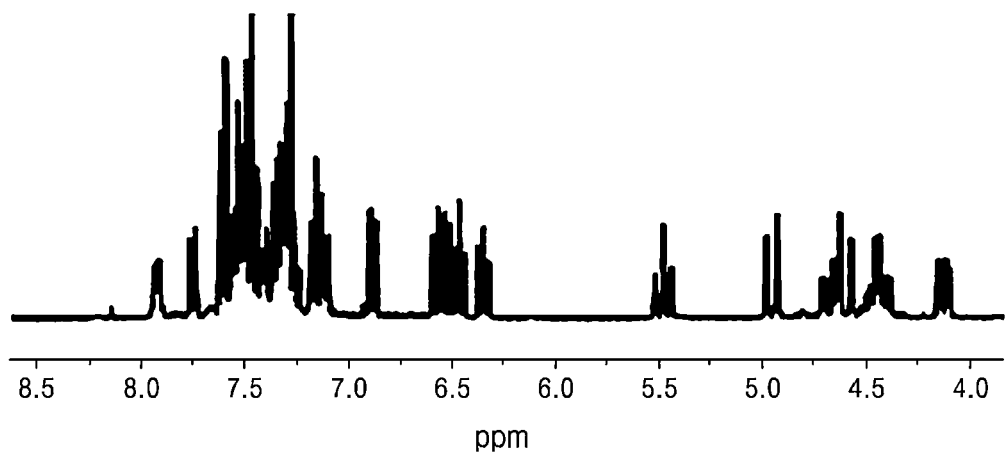
FIGS. 6A to 6C show $^1$H NMR spectra of 2:1 adduct formation (FIG. 6A), 1:1 adduct formation (FIG. 6B), and 1:5 adduct formation (FIG. 6C), respectively, by reaction of Compound 1 and alaninol(=amino propanol), according to an example of the present disclosure.
Figure 6B:
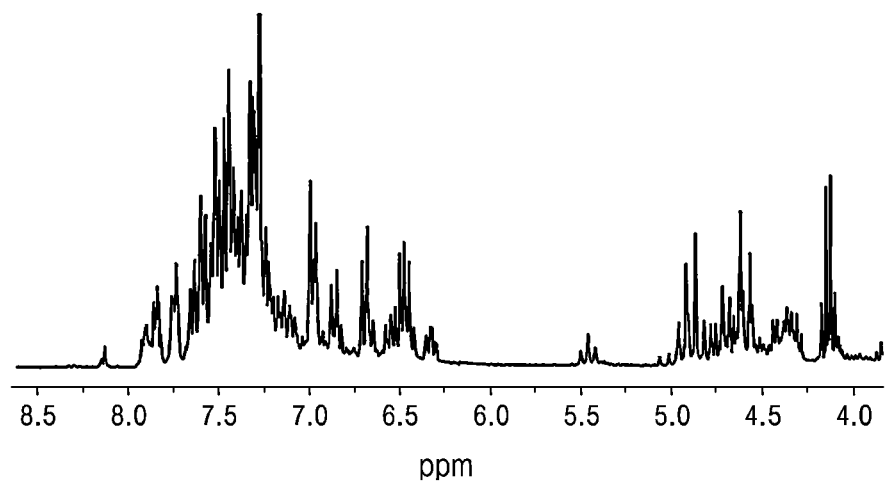
Figure 6C:
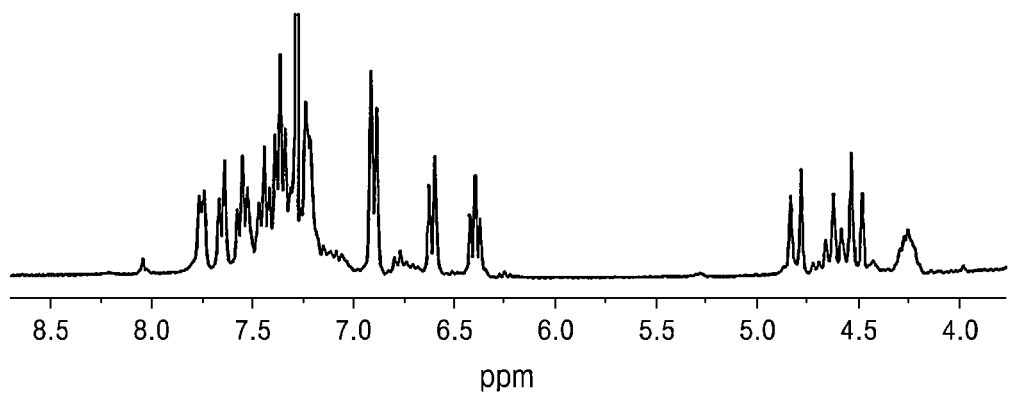
Figure 6D:
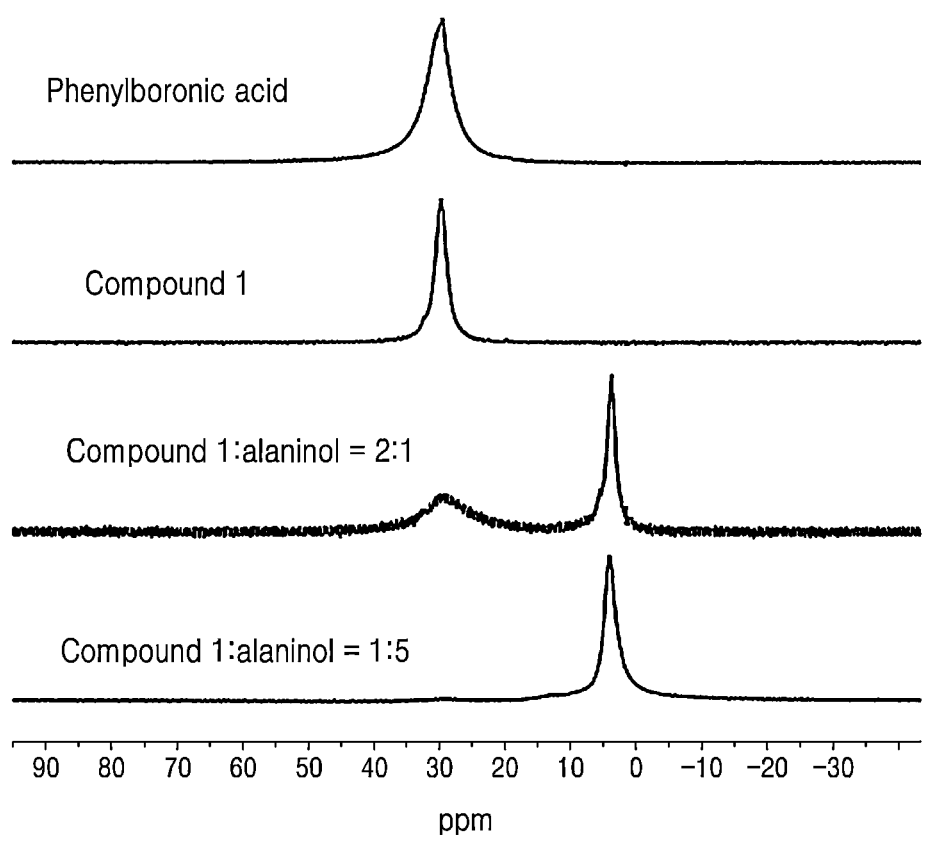
FIG. 6D shows $^{11}$B NMR spectra by reaction of Compound 1 and alaninol with changing equivalent, according to an example of the present disclosure.
Figure 6E:
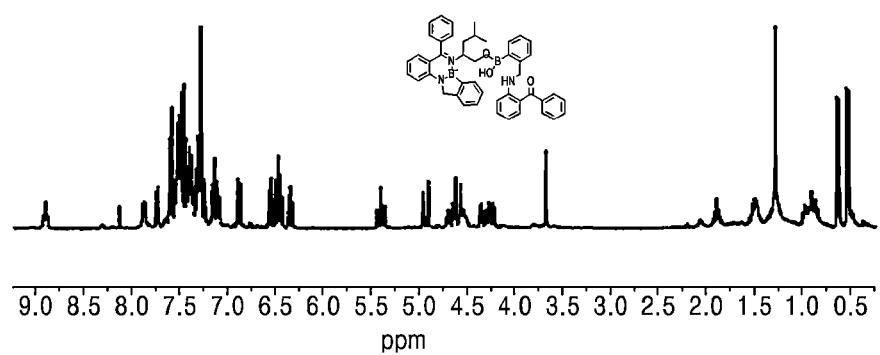
FIGS. 6E(i) to 6E(iv) show $^1$H NMR spectra of 2:1 adduct formation by reaction of Compound 1 and other aminoalcohol, respectively, according to an example of the present disclosure.
Figure 6E:
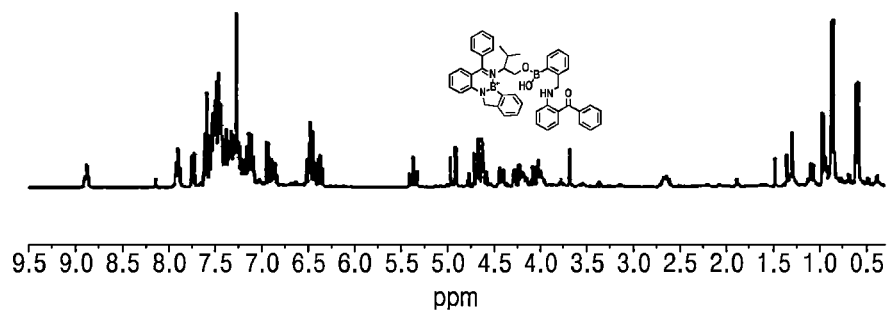

Referring to FIGS. 4A and 4B, ¹¹B NMR spectrum of 1:1 adduct formation by reaction of Compound 1 and ethanolamine (4A), and ¹¹B NMR spectrum of Compound 1 (4B) can be seen.

Referring to FIGS. 6A to 6C, FIG. 6D, and FIGS. 6E(i) to 6E(iv), ¹H NMR spectrum of 2:1 adduct formation (6A), ¹H NMR spectrum of 1:1 adduct formation (6B), ¹H NMR spectrum of 1:5 adduct formation (6C), by reaction of Compound 1 and alaninol(=amino propanol), 11B NMR spectra by reaction of Compound 1 and alaninol with changing equivalent (6D), and ¹H NMR spectra of 2:1 adduct formation by reaction of Compound 1 and other aminoalcohol (6E) can be seen.

When 1 eq of alaninol was added, ¹H NMR shows a very complex pattern unlike ethanolamine.

Compound 1 shows a different reactivity depending on steric properties of carbon connected to an amine group. Ethanolamine does not have a steric hindrance and thus forms a 1:1 adduct with Compound 1 in a very short time (FIGS. 2A and 2B, FIGS. 3A and 3B, and FIGS. 4A and 4B). Meanwhile, alaninol has a steric hindrance and thus forms a 2:1 (Compound 1: alaninol) adduct instead of a 1:1 adduct, and when the equivalent of alaninol increases, a 1:1 to 1:2 adduct is formed (FIGS. 6A to 6C, FIG. 6D, and FIGS. 6E(i) to 6E(iv)).

Fluorescence is also slightly different for each kind of amine compound including aminoalcohol. In particular, a CD spectrum is remarkably different for each kind of aminoalcohol. This shows that if Compound 1 is used as a probe, it is possible to identify even the type of a substrate (Reaction Scheme 4).

Comparative Example 1: Synthesis of Comparative Compound 1

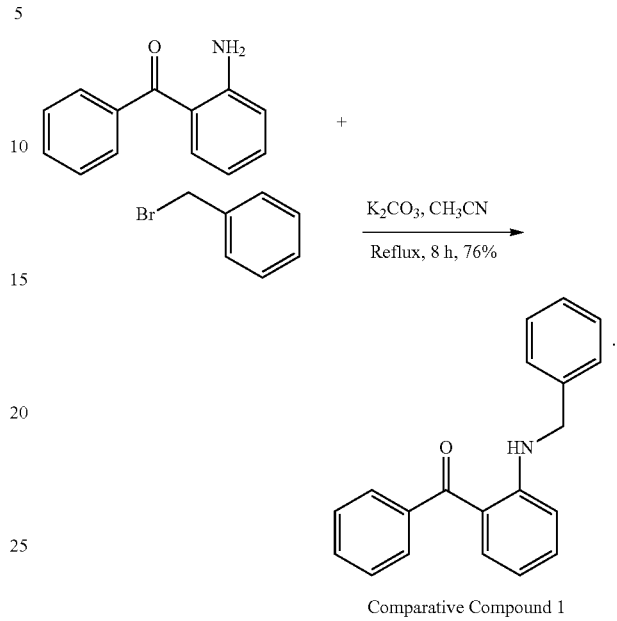

Comparative Compound 1

2-aminobenzophenone (0.10 g, 0.51 mmol), benzylbromide (0.24 g, 1.4 mmol) and potassium carbonate (0.17 g, 1.2 mmol) were added into acetonitrile (1.5 mL) and refluxed for 8 hours. Compound 2 (0.083 g, 0.29 mmol) was obtained by silica gel column chromatography using EA/hexane (1/50) as a developer.

Yield: 57%. ¹H NMR (300 MHz, CDCl₃): δ 9.11; (t, J=3 Hz, 1H), δ 7.72-6.59; (m, 14H), δ 4.58; (d, J=6 Hz, 2H).

As a comparative example, referring to FIGS. 5A to 5D, ¹H NMR spectrum of 1:5 adduct formation by reaction of Comparative Compound 1 and ethanolamine (5A), ¹H NMR spectrum of Comparative Compound 1 (5B), ¹H NMR spectrum of 1:5 adduct formation by reaction of Comparative Compound 2 and ethanolamine (5C), and ¹H NMR spectrum of Comparative Compound 2 (5D) can be seen. FIGS. 5A to 5D show the reactivity of Comparative Compound 1 which is similar to the Compound 1 but does not contain boron, Comparative Compound 2 substituted with an uryl group instead of boron, and aminoalcohol. It can be seen that in the absence of boron, no reaction occurs with aminoalcohol. It can be seen that the uryl group has properties as a Lewis acid like boron but does not contribute to the formation of imine.

Comparative Example 2: Synthesis of Comparative Compound 2

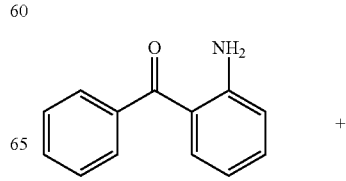

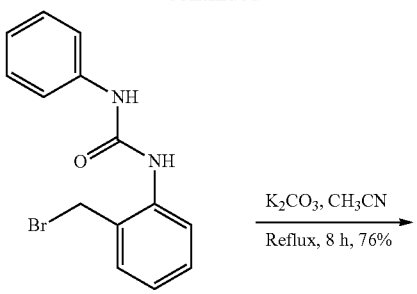

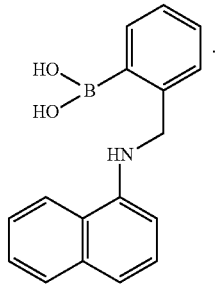

Comparative Compound 3

2-(bromomethyl) phenyl boronic acid (0.150 g, 0.70 mmol) and potassium carbonate (0.19 g, 1.37 mmol) in ACN (1.5 mL) were put into 1-naphthylamine (0.10 mg, 0.70 mmol) and stirred at room temperature for 8 hours. Comparative compound 3 (0.04 g, 0.14 mmol) was obtained by silica gel column chromatography using EA/hexane (1:9) as a developer.

Yield: 20%. $^1$H NMR (300 MHz, CD$_3$CN): δ 7.98-6.79; (m, 11H), δ 4.53; (s, 2H).

Example 5: Fluorescent Imaging Test of Mitochondria Using Compound 1

HeLa cells were incubated with 10 μM probes for 30 minutes and the residual probes were removed. Thereafter, (a) 0 μM, (b) 10 μM, (c) 100 μM and (d) 1,000 μM of ethanolamine were added for 30 minutes, followed by washing with DPBS to show a fluorescent image of the mitochondria in the cells through confocal microscopy (excitation wavelength: 405 nm/emission wavelength: 490 nm to 590 nm).

Figure 7A:
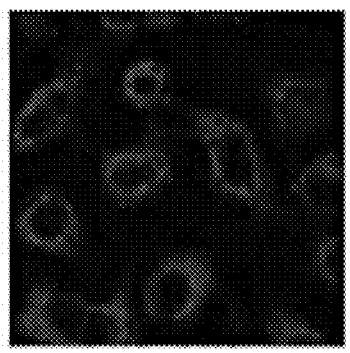
FIGS. 7A (i) to 7D (ii) show fluorescence images of mitochondria in a cell acquired by confocal microscopy after HeLa cells were incubated with 10 μM probe in acetonitrile solution and then added 0 μM ethanolamine (FIGS. 7A (i) and (ii)), 10 μM ethanolamine (FIGS. 7B(i) and 7B(ii)), 100 μM ethanolamine (FIGS. 7C (i) and (ii)) and 1000 μM ethanolamine (FIGS. 7D (i) and (ii)), respectively, according to an example of the present disclosure.
Figure 7A:
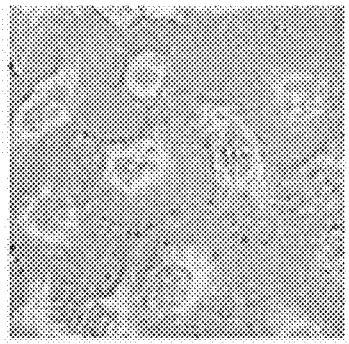
Figure 7B:
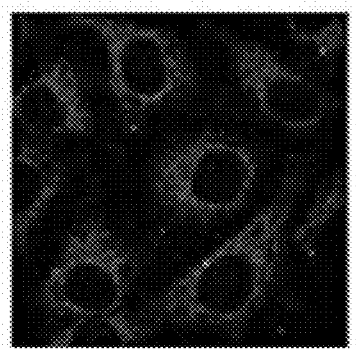
Figure 7B:
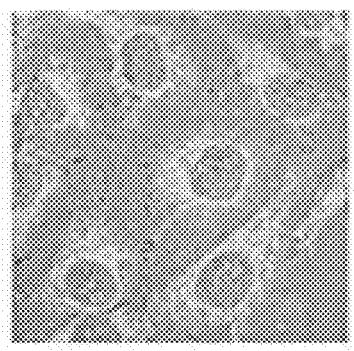
Figure 7C:
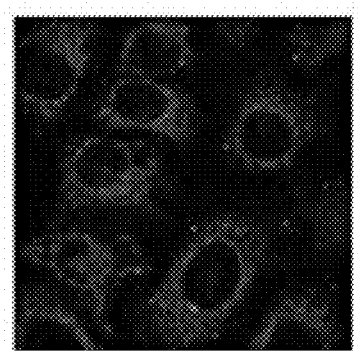
Figure 7C:
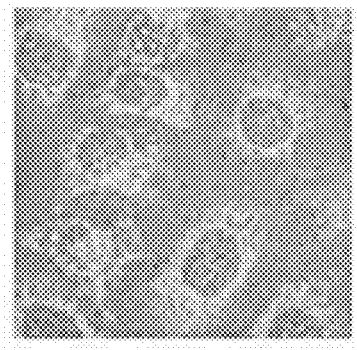
Figure 7D:
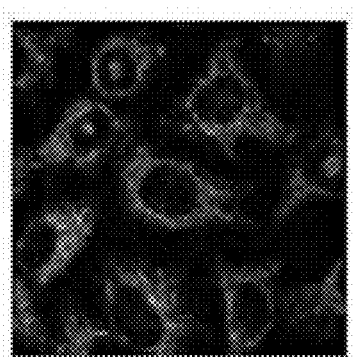
Figure 7D:
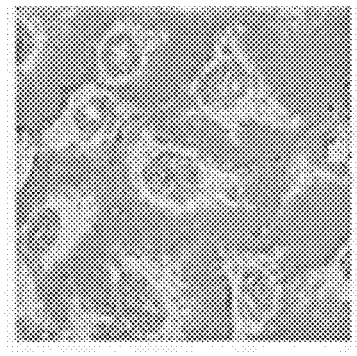

Referring to FIGS. 7A (i) to 7D (ii), it can be seen that HeLa cells were incubated with 10 μM probes for 30 minutes in an acetonitrile solution and the residual probes were removed and then, 0 μM (FIGS. 7A (i)-(ii)), 10 μM (FIGS. 7B (i)-(ii)), 100 μM (FIGS. 7C (i)-(ii)) and 1,000 μM (FIGS. 7D (i)-(ii)) of ethanolamine were added for 30 minutes, followed by washing with DPBS to show a fluorescent image of the mitochondria in the cells observed by confocal microscopy.

Figure 8A:
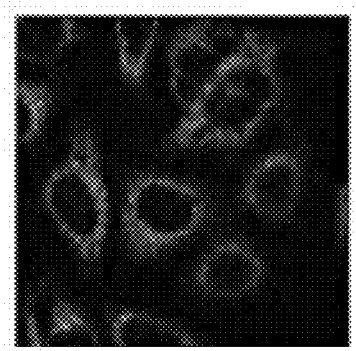
FIGS. 8A (i) to 8D (ii) show fluorescence images of mitochondria in a cell acquired by confocal microscopy after HeLa cells were incubated with 10 μM probe in dimethyl sulfoxide solution and then added 0 μM ethanolamine (FIGS. 8A (i) and (ii)), 10 μM ethanolamine (FIGS. 8B (i) and (ii)), 100 μM ethanolamine (FIGS. 8C (i) and (ii)), and 1000 μM ethanolamine (FIGS. 8D (i) and (ii)), respectively, according to an example of the present disclosure.
Figure 8A:
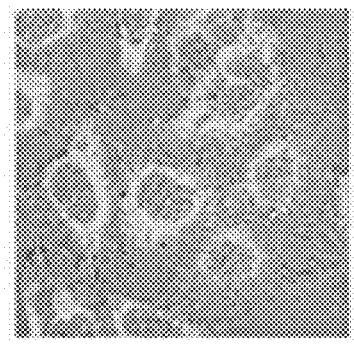
Figure 8B:
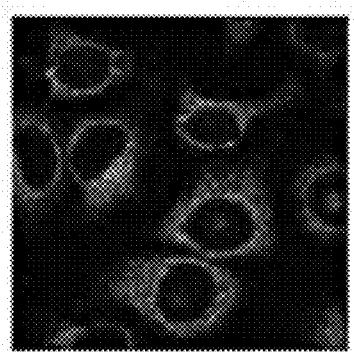
Figure 8B:
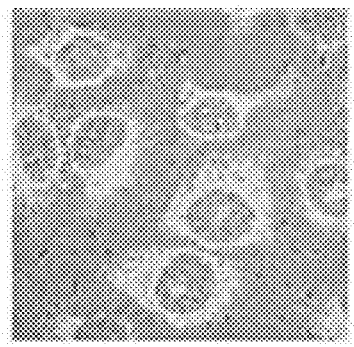
Figure 8C:
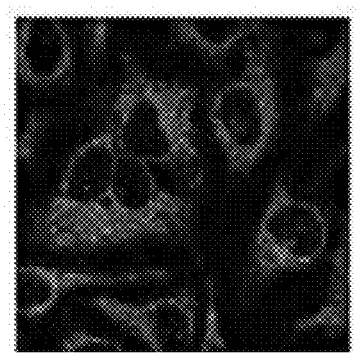
Figure 8C:
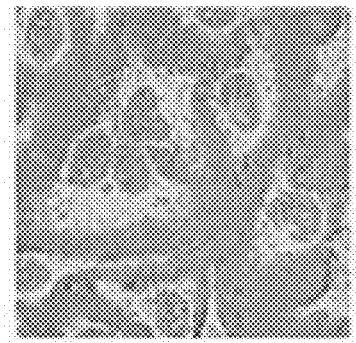
Figure 8D:
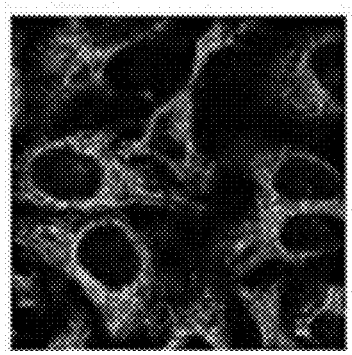
Figure 8D:
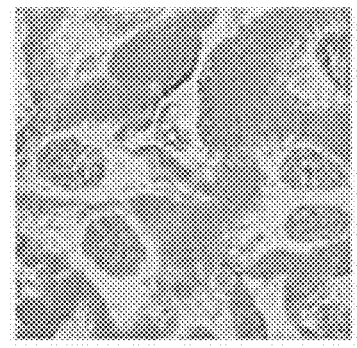

Referring to FIGS. 8A (i) to 8D (ii), it can be seen that HeLa cells were incubated with 10 μM probes for 30 minutes in a DMSO solution and the residual probes were removed and then, 0 μM (FIG. 8A (i)-(ii)), 10 μM (FIG. 8B (i)-(ii)), 100 μM (FIG. 8C (i)-(ii)) and 1,000 μM (FIG. 8D (i)-(ii)) of ethanolamine were added for 30 minutes, followed by washing with DPBS to show a fluorescent image of the mitochondria in the cells observed by confocal microscopy.

Example 6: Fluorescent Imaging Test of Mitochondria Using Compound 1-Uncoupler Process HeLa cells were incubated with (a) 10 μM probes and (b) 10 μM probes+40 μM CCCP for 30 minutes and washed with DPBS to show a fluorescent image of the mitochondria in the cells through confocal microscopy (excitation wavelength: 405 nm/emission wavelength: 490 nm to 590 nm).

Figure 9A:
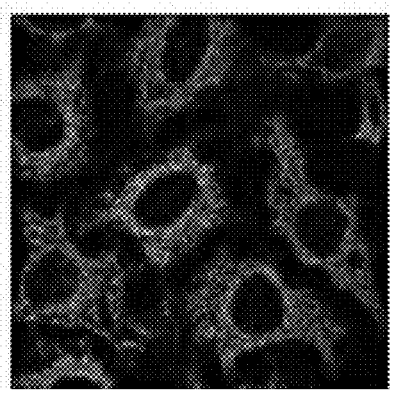
FIGS. 9A (i) to 9B (ii) show fluorescence images of mitochondria in a cell acquired by confocal microscopy after HeLa cells were incubated with 10 μM probe (FIGS. 9A (i) and (ii)), and 10 μM probe+40 μM CCCP (FIGS. 9B (i) and (ii)), respectively, for 30 min, according to an example of the present disclosure.
Figure 9A:
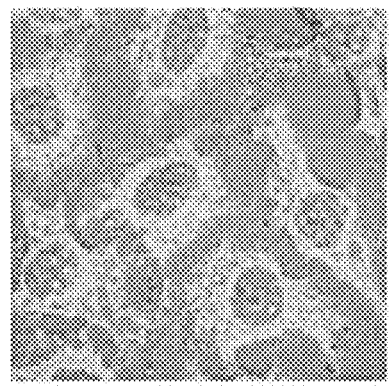

FIG. 9A (i) to 9B (ii) show fluorescence images of mitochondria in a cell acquired by confocal microscopy after HeLa cells were incubated with 10 μM probe (FIG. 9A

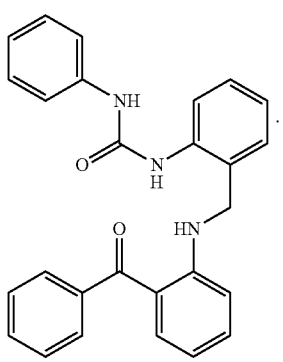

Comparative Compound 2

1-bromomethyl-2-phenylurylbenzene (0.92 g, 3.0 mmol) compound and potassium carbonate (0.41 g, 3.0 mmol) in ACN (3 mL) were put into 2-aminobenzophenone (0.50 g, 2.5 mmol) and stirred at 85° C. for 8 hours. The progress of the reaction was monitored by TLC test, and Comparative Compound 2 (0.60 mg, 1.4 mmol) was obtained by silica gel column chromatography using EA/hexane (1:9) as a developer.

Yield: 56%. $^1$H NMR (300 MHz, CDCl$_3$): δ 8.91; (br, 1H), δ 7.62-6.57; (m, 20H), δ 4.34; (s, 2H).

Comparative Example 3: Synthesis of Comparative Compound 3

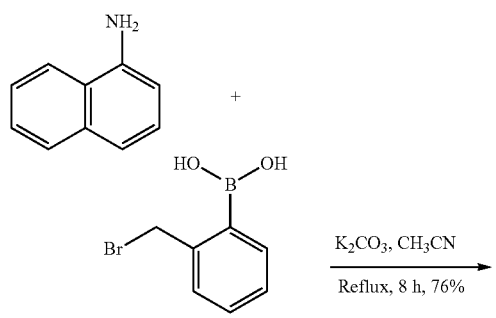

Figure 9B:
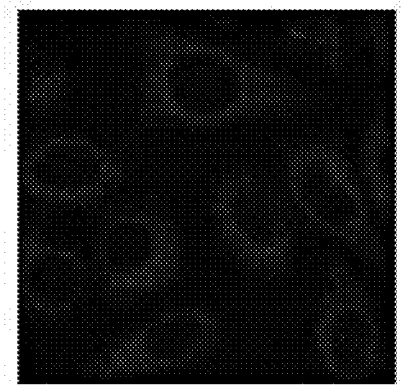
Figure 9B:
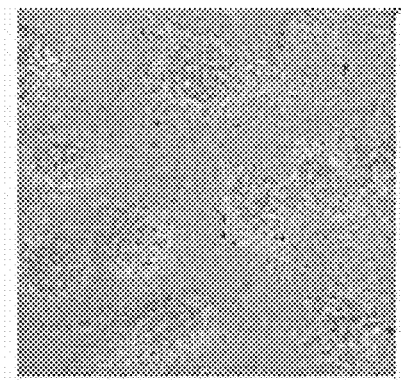
Figure 10A:
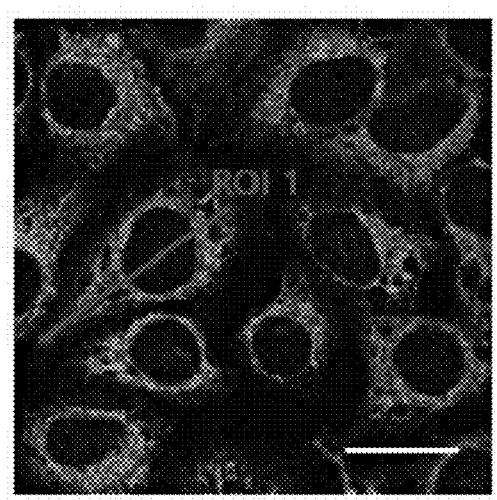
FIGS. 10A to 10C show fluorescence images of mitochondria in a cell by Compound 1 (excitation at 405 nm/emission at 490 nm to 590 nm) (FIG. 10A), Mitotracker Deep Red (excitation at 635 nm/emission at 655 nm to 755 nm) (FIG. 10B), and Compound 1 and Mitotracker Deep Red merged (FIG. 10C), respectively, acquired by confocal microscopy after HeLa cells were incubated with 10 μM Compound 1 and 50 nM Mitotracker Deep Red for 30 min, according to an example of the present disclosure.
Figure 10B:
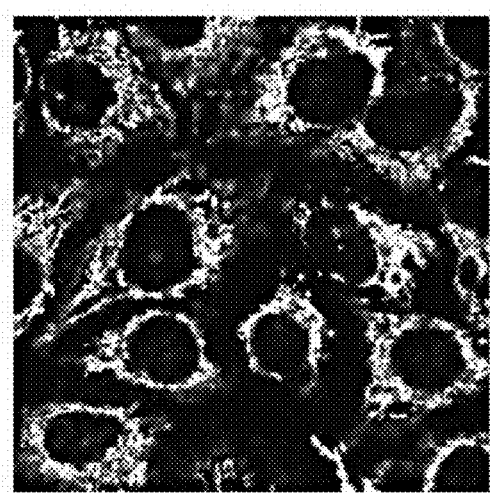
Figure 10C:
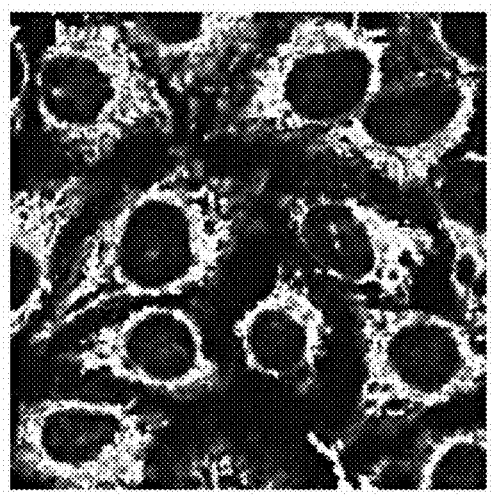
Figure 10D:
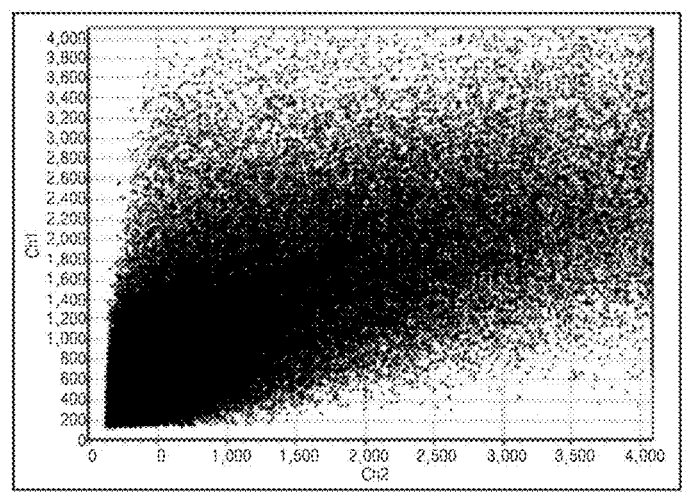
FIG. 10D shows colocalization analysis graph of Compound 1 and Mitotracker Deep Red (Ch 1: Compound 1, Ch 2: Mitotracker Deep Red), according to an example of the present disclosure.
Figure 10E:
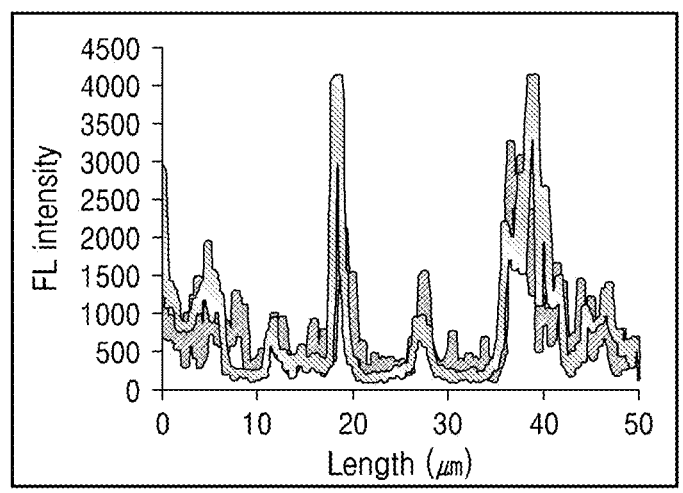
FIG. 10E shows fluorescence intensity profile of ROI 1 (region of interest) in the FIG. 10A (dark gray line: Compound 1, light gray line: Mitotracker Deep Red, Scale bar: 20 μm, Pearson's coefficient: 0.81±0.02), according to an example of the present disclosure.

(i)-(ii)), and 10 μM probe+40 μM CCCP (FIG. 9B (i)-(ii)), respectively, for 30 min, washed with DPBS. It can be seen that the experimental results of treating the mitochondria in the cells with cccp, which is an uncoupler, and imaging the cells using the probe of Compound 1 are shown.

Example 7: Comparison of Fluorescent Image of Mitochondria Using Compound 1 and MitoTracker Deep Red Referring to FIGS. 10A to 10E, HeLa cells were incubated with 10 μM Compound 1 and 50 nM MitoTracker Deep Red for 30 minutes and a fluorescent image of the mitochondria in the cells was obtained by confocal microscopy. The fluorescent image of the mitochondria obtained using Compound 1 and MitoTracker Deep Red showed a degree of agreement of about 81% (Pearson correlation coefficient: 0.81±0.02).

Figure 11A:
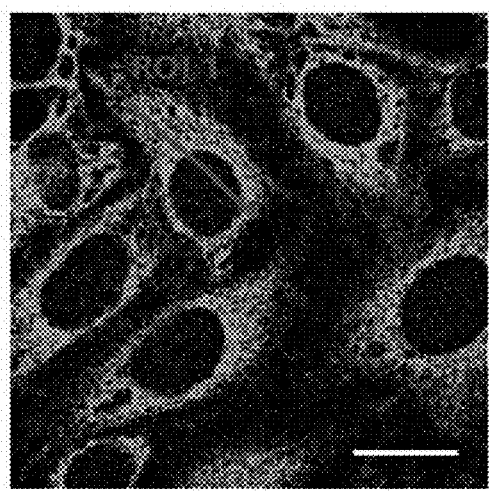
FIGS. 11A to 11C show fluorescence images of mitochondria in a cell by Compound 1 (excitation at 405 nm/emission at 490 nm to 590 nm) (FIG. 11A), ER(endoplasmic reticulum)-tracker Red (excitation at 559 nm/emission at 576 nm to 675 nm) (FIG. 11B), and Compound 1 and ER-tracker Red merged (FIG. 11C), respectively, acquired by confocal microscopy after HeLa cells were incubated with 10 μM Compound 1 and 1 μM ER-tracker Red for 30 min, according to an example of the present disclosure.
Figure 11B:
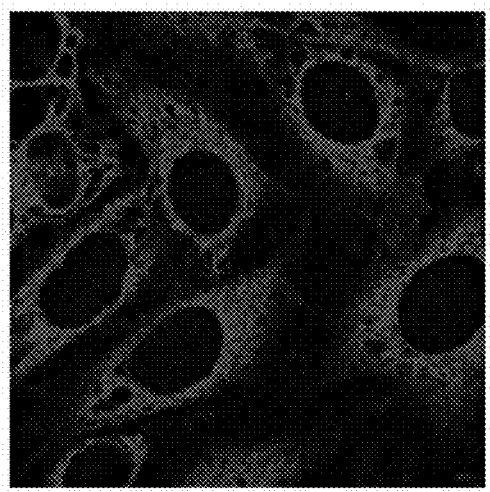
Figure 11C:
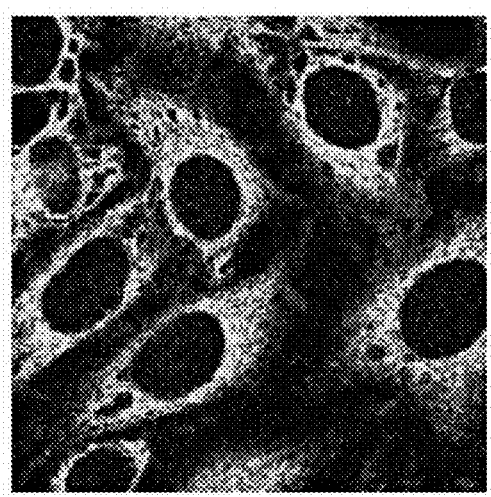
Figure 11D:
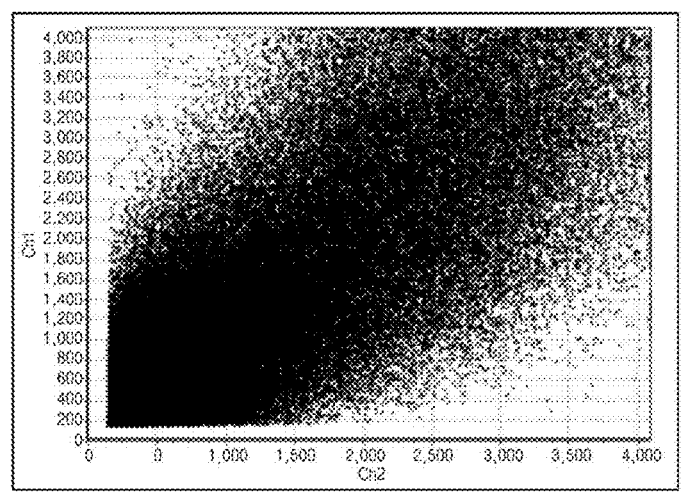
FIG. 11D shows colocalization analysis graph of Compound 1 and ER-tracker Red (Ch 1: Compound 1, Ch 2: ER-tracker Red), according to an example of the present disclosure.
Figure 11E:
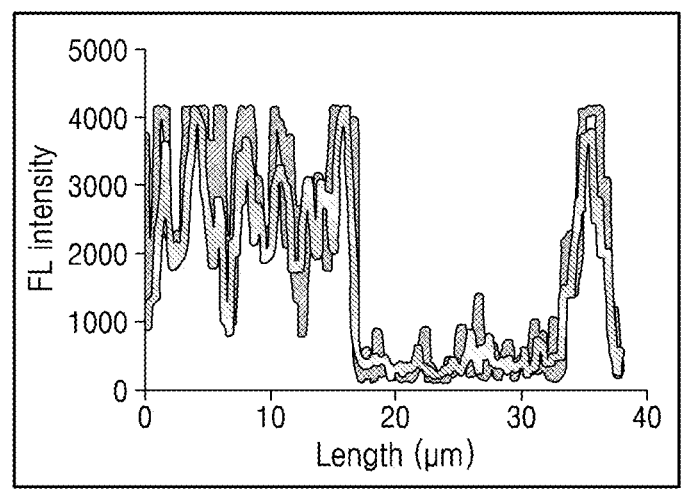
FIG. 11E shows fluorescence intensity profile of ROI 1 in the FIG. 11A (dark gray line: Compound 1, light gray line: ER-tracker Red, Scale bar: 20 μm, Pearson's coefficient: 0.85±0.01), according to an example of the present disclosure.

Example 8: Comparative Experiment of Fluorescent Imaging of Mitochondria Using Compound 1 and Endoplasmic Reticulum (ER)-Tracker Red Referring to FIGS. 11A to 11C, HeLa cells were incubated with 10 μM Compound 1 and 1 μM ER-Tracker Red for 30 minutes and a fluorescent image of the mitochondria in the cells was obtained by confocal microscopy. The fluorescent image of the mitochondria obtained using Compound 1 and ER-Tracker Red showed a degree of agreement of about 85% (Pearson correlation coefficient: 0.85±0.01).

Figure 12A:
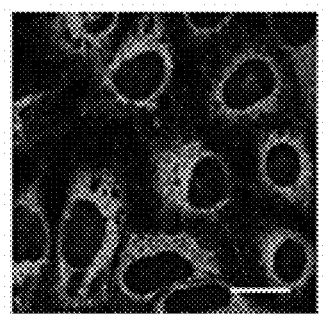
FIGS. 12A(i) to 12A(viii) show fluorescence images of mitochondria in a cell by Compound 1 (top) and Mitotracker Deep Red (bottom), acquired by confocal microscopy after HeLa cells were co-stained with 10 μM Compound 1 and 50 nM Mitotracker Deep Red for 30 min, according to an example of the present disclosure.
Figure 12A:
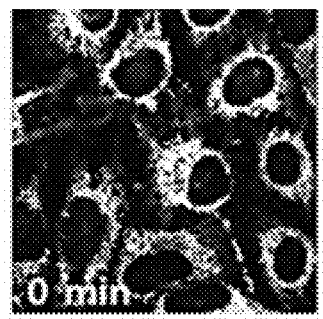
Figure 12A:
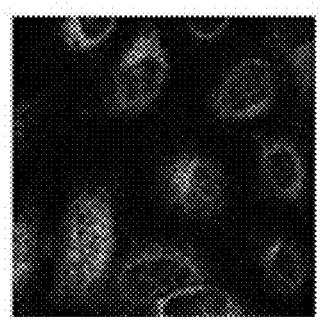
Figure 12A:
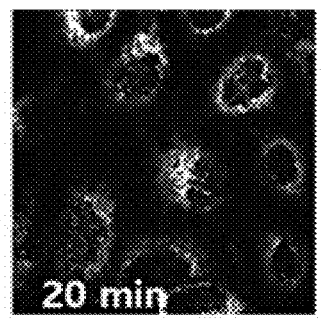
Figure 12B:
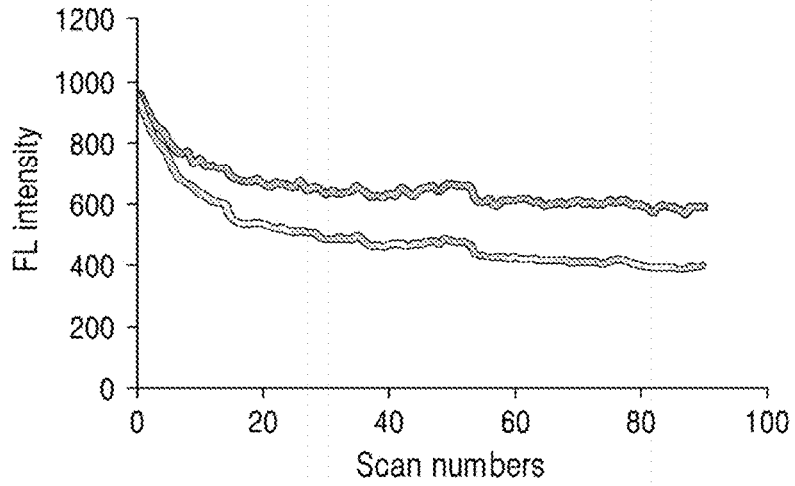
FIG. 12B shows fluorescence intensity profile of mitochondria by scan numbers (dark gray line: Compound 1, light gray line: Mitotracker Deep Red), acquired by confocal microscopy after HeLa cells were co-stained with 10 μM Compound 1 and 50 nM Mitotracker Deep Red for 30 min, according to an example of the present disclosure.

Example 9: Comparative Experiment of Photostability of Mitochondrial Fluorescence Using Compound 1 and MitoTracker Deep Red Referring to FIGS. 12A(i) to 12A(viii) and FIG. 12B, in order to compare photostability of mitochondrial fluorescence using Compound 1 and MitoTracker Deep Red, HeLa cells were co-stained with each of 10 μm Compound 1 and 50 nM MitoTracker Deep Red for 30 minutes, and fluorescence images and fluorescence intensity were obtained by scanning 90 times (20 sec/scan). The fluorescence intensity was analyzed by Olympus Fluoview Ver.4.0b software. The photostability of Compound 1 was checked based on the fluorescent images and fluorescence intensity depending on the number of scans and time. Referring to FIG. 12B, the fluorescence intensity of Compound 1 was higher than that of MitoTracker Deep Red.

Example 10: Cytotoxicity Test of Compound 1

Figure 13:
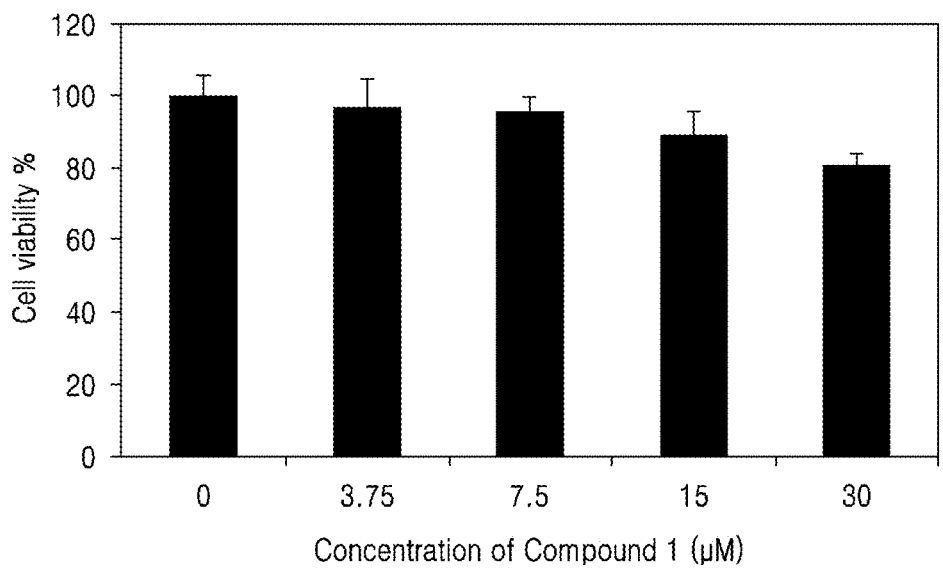
FIG. 13 shows cell viability according concentration of Compound 1 obtained after culturing HeLa cells treated with various concentrations of Compound 1 for 24 hours in a medium containing MTT for 4 hours, according to an example of the present disclosure.
Figure 14A:
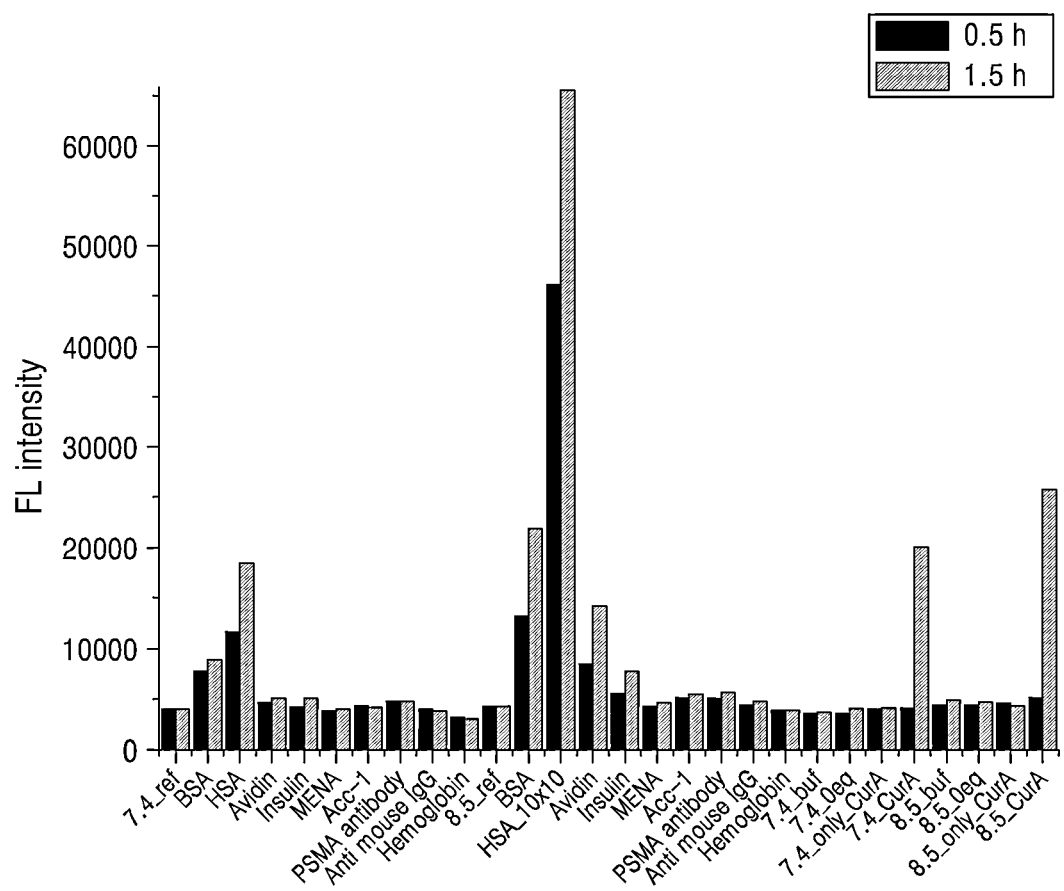
FIG. 14A shows fluorescence (FL) intensity profile measured after incubating 3 μM Compound 1 with various proteins in DMSO for 0.5 hours and 1.5 hours, respectively (slit: 10 nm×20 nm, λex=410 nm), according to an example of the present disclosure.
Figure 14B:
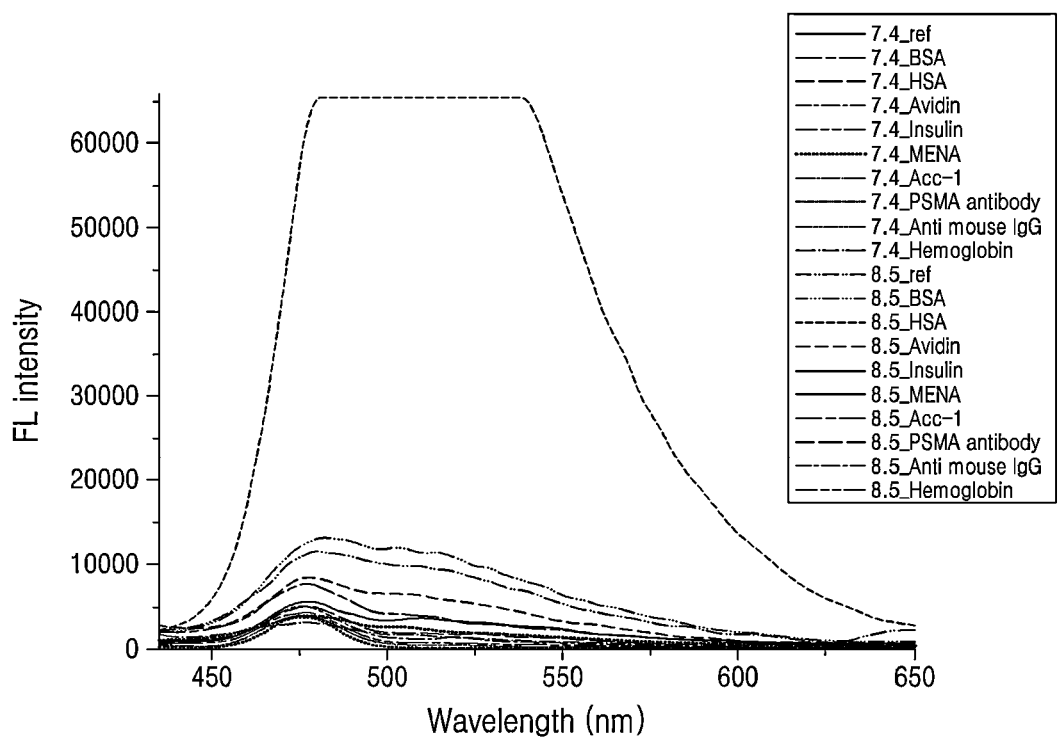
FIG. 14B shows FL intensity profile by protein and condition (pH) measured after incubating 3 μM Compound 1 with various proteins in DMSO for 0.5 hours (slit: 10 nm×20 nm, λex=410 nm), according to an example of the present disclosure.
Figure 14C:
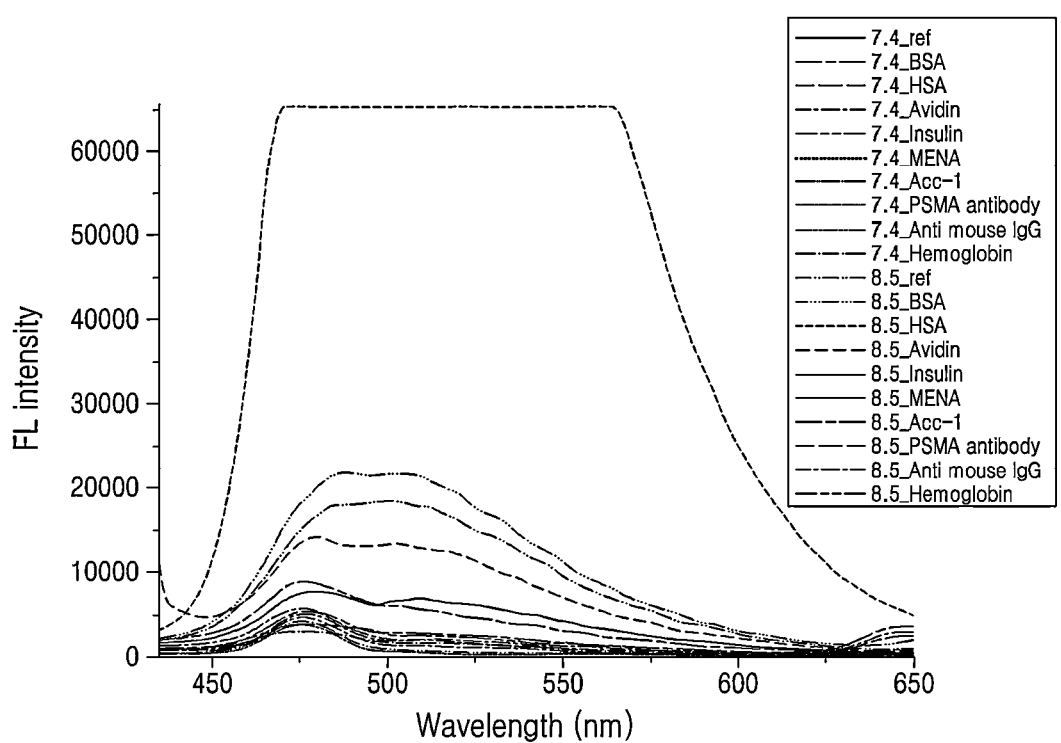
FIG. 14C shows FL intensity profile by protein and condition (pH) measured after incubating 3 μM Compound 1 with various proteins in DMSO for 1.5 hours (slit: 10 nm×20 nm, λex=410 nm), according to an example of the present disclosure.
Figure 14D:
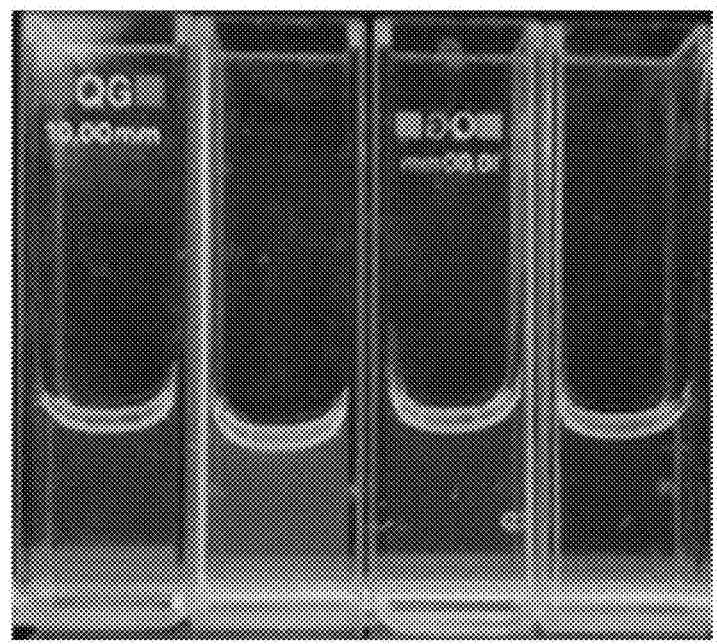
FIGS. 14D(i) to 14D(vi) show fluorescence imaging of proteins measured after incubating 3 μM Compound 1 with various proteins in DMSO for 0.5 hours and 1.5 hours, respectively (λex=410 nm), according to an example of the present disclosure.
Figure 14D:
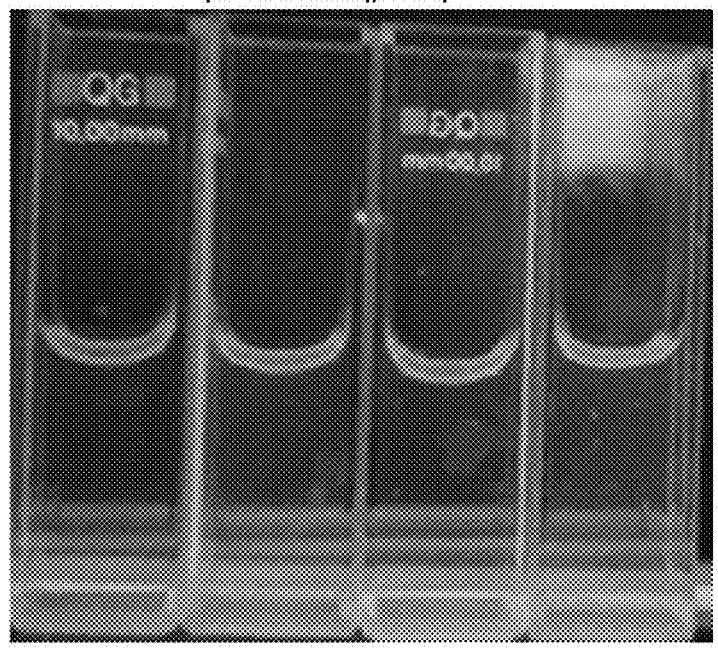

Referring to FIG. 13, HeLa cells were treated with various concentrations of Compound 1 for 24 hours, cultured in a medium containing MTT for 4 hours, and then the viability of the cells depending on the concentration of Compound 1 was checked. When the absorbance of a sample not treated with Compound 1 was set to 100%, it was confirmed that the cells treated with 30 μM Compound 1 survived about 80%.

Example 11: Comparative Experiment of Fluorescent Imaging of Protein Using Compound 1

After 3 μM Compound 1 and various types of proteins in DMSO were incubated for 0.5 hours and 1.5 hours, fluorescence intensity profiles and fluorescent images depending on the types of proteins were compared.

Referring to FIGS. 14A to FIG. 14C and FIGS. 14D(i) to 14D(vi), it was confirmed that Compound 1 exhibits fluorescent imaging performance and selectivity specific to HSA.

Example 12: Comparison of Fluorescent Imaging of HSA Protein Using Compound 1 at Various pH Values After Compound 1 and HSA protein were incubated in buffer solutions at various pH values, fluorescence intensity profiles and fluorescent images depending on pH were compared.

Figure 15A:
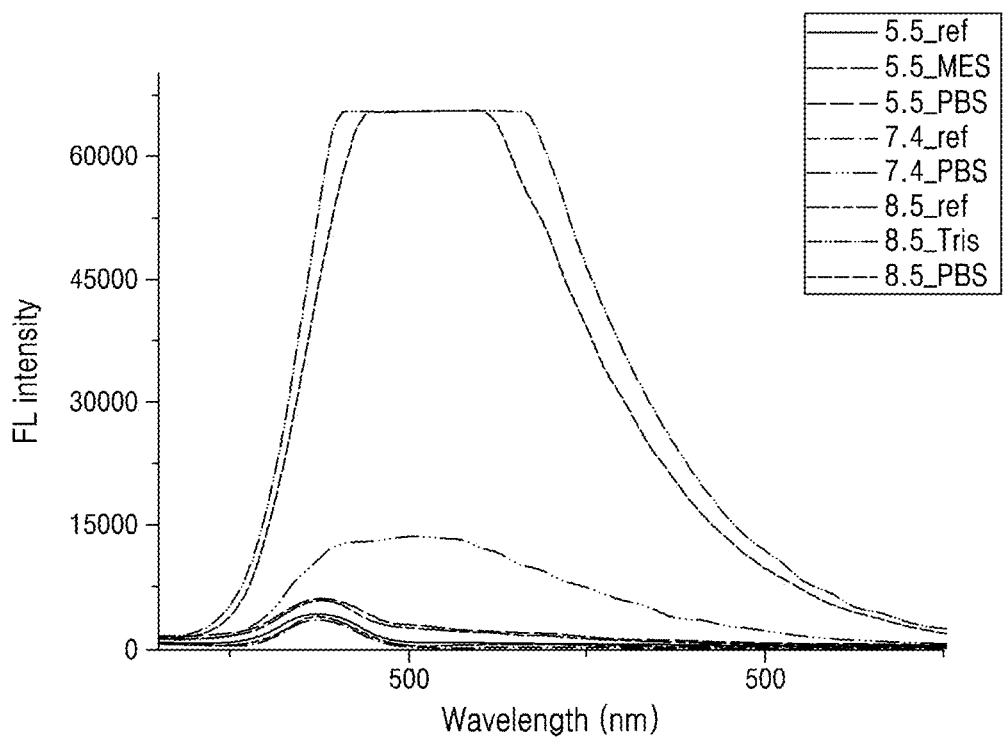
FIG. 15A shows fluorescence intensity profile measured after each incubating Compound 1 with HSA protein in buffer solution of various pH, according to an example of the present disclosure.
Figure 15B:
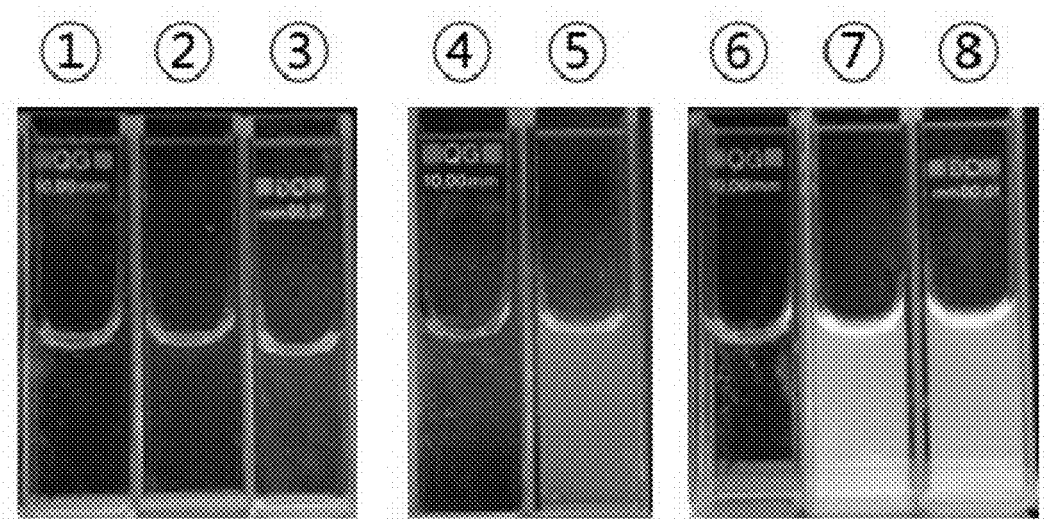
FIG. 15B shows fluorescence imaging measured after each incubating Compound 1 with HSA protein in buffer solution of various pH (from left ① ref, MES buffer, pH 5.5, ② HSA in MES buffer, pH 5.5, ③ HSA in PBS buffer pH 5.5, ④ ref, PBS buffer, pH 7.5, ⑤ HSA in PBS buffer, pH 7.5, ⑥ ref, Tris buffer, pH 8.5, ⑦ HSA in Tris buffer, pH 8.5, ⑧ HSA in PBS buffer, pH 8.5), according to an example of the present disclosure.
Figure 16:
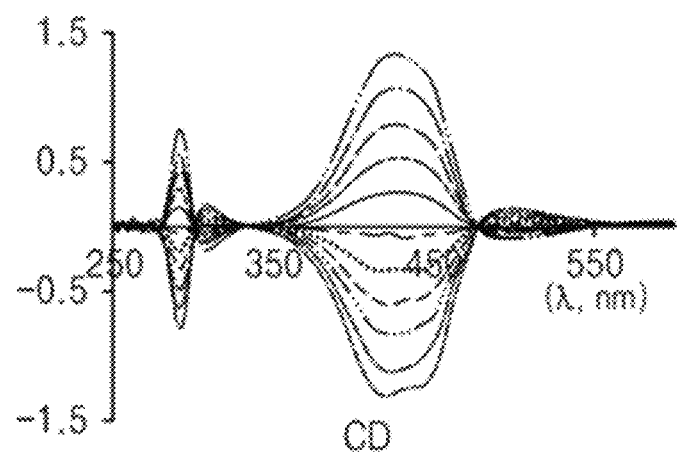
FIG. 16 shows CD spectrum of Compound 1 reacted with aminoalcohol.
Figure 17:
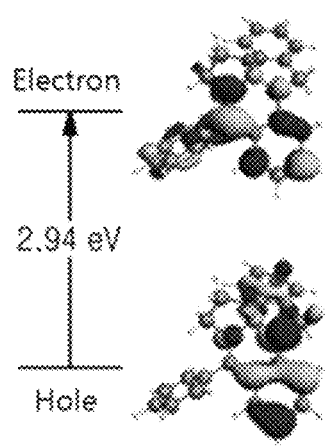
FIG. 17 shows scheme of delocalized It (bottom) and π* (top) orbitals of Compound 1 And FIG. 18 shows fluorescence spectra trend for Compound 1 reacted with aminoalcohol.
Figure 18:
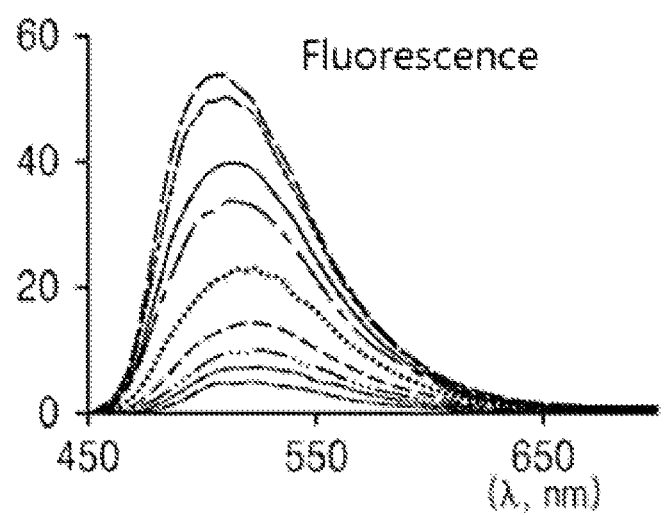

Referring to FIG. 15A and FIG. 15B, Compound 1 at pH 7.4, pH 7.5 and pH 8.5 showed fluorescent imaging performance specific to HSA protein.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A composition for cell imaging, comprising a probe compound represented by the following Chemical Formula 1:

[Chemical Formula 1]

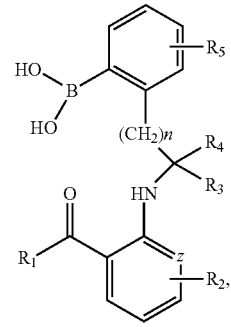

wherein,
$R_1$ is selected from the group consisting of hydrogen, a halogen group, an amino group, a $C_{1-10}$ alkyl group, a $C_{6-10}$ aryl group and a $C_{1-10}$ alkoxy group,
each of $R_3$ and $R_4$ is independently selected from the group consisting of hydrogen, a halogen group, a $C_{1-10}$ alkyl group, a $C_{6-10}$ aryl group and a $C_{1-10}$ alkoxy group,
each of $R_2$ and $R_5$ is independently selected from the group consisting of hydrogen, a halogen group, an amino group, a nitro group, a cyano group, a formyl group, a carboxyl group, a $C_{1-10}$ alkyl group, a $C_{1-10}$ alkylcarbonyl group, a $C_{6-10}$ aryl group and a $C_{1-10}$ alkoxy group, when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, a hydroxy group, an amino group, a cyano group, a nitro group and a $C_{6-10}$ aryl group, Z is =N— or =CH—, and n is an integer of from 0 to 5.

2. The composition of claim 1, wherein the probe compound comprises at least one of the following compounds:

[Compound 1]

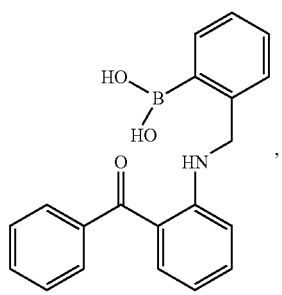

[Compound 2]

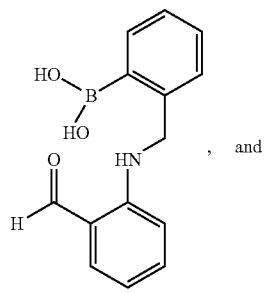, and

[Compound 3]

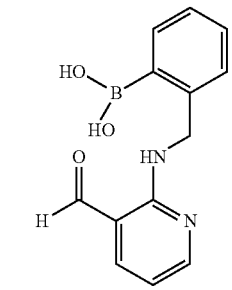

3. The composition of claim 1, wherein the composition for cell imaging is used to image a material in a living cell.

4. The composition of claim 3, wherein the material in the cell comprises a cell-material or an organelle, and the cell-material includes DNA, protein, $Hg^{2+}$, $Cu^{2+}$, adenosine triphosphate (ATP), amino acid, or reactive oxygen species (ROS).

5. The composition of claim 4, wherein the organelle is mitochondria so that stem cells or cancer cells are imaged.

6. The composition of claim 3, wherein the material in the cell includes cytoplasm, mitochondria, proteins or biomolecules.

7. The composition of claim 3, wherein the material in the cell includes a biomaterial selected from the group consisting of an amino acid, a nucleotide, an amino acid ester, an amino acid amide, an amino alcohol, and combinations thereof.

8. The composition of claim 1, wherein the composition selectively senses a cell containing human serum albumin (HSA).

9. A method of cell-material imaging, comprising:

measuring fluorescence generated by reacting a probe compound represented by the following Chemical Formula 1, and a material in a target cell:

[Chemical Formula 1]

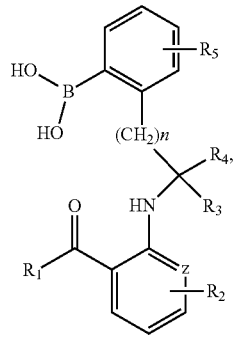

wherein, $R_1$ is selected from the group consisting of hydrogen, a halogen group, an amino group, a $C_{1-10}$ alkyl group, a $C_{6-10}$ aryl group and a $C_{1-10}$ alkoxy group, each of $R_3$ and $R_4$ is independently selected from the group consisting of hydrogen, a halogen group, a $C_{1-10}$ alkyl group, a $C_{6-10}$ aryl group and a $C_{1-10}$ alkoxy group, each of $R_2$ and $R_5$ is independently selected from the group consisting of hydrogen, a halogen group, an amino group, a nitro group, a cyano group, a formyl group, a carboxyl group, a $C_{1-10}$ alkyl group, a $C_{1-10}$ alkylcarbonyl group, a $C_{6-10}$ aryl group and a $C_{1-10}$ alkoxy group, when the $C_{1-10}$ alkyl group, the $C_{1-10}$ alkylcarbonyl group, the $C_{6-10}$ aryl group or the $C_{1-10}$ alkoxy group is substituted, it is substituted with at least one substituent selected from the group consisting of a halogen group, a hydroxy group, an amino group, a cyano group, a nitro group and a $C_{6-10}$ aryl group, Z is =N— or =CH—, and n is an integer of from 0 to 5.

10. The method of claim 9, wherein the target cell is a living cell.

11. The method of claim 9, further comprising:

obtaining an image of the material in the target cell by measuring fluorescence generated by reacting the probe compound and the material in the target cell.

12. The method of claim 9, wherein the material in the target cell comprises a cell-material or an organelle, and the cell-material includes DNA, protein, $Hg^{2+}$, $Cu^{2+}$, adenosine triphosphate (ATP), amino acid, or reactive oxygen species (ROS).

13. The method of claim 12, wherein the organelle is mitochondria so that stem cells or cancer cells are imaged.

14. The method of claim 9,
wherein the material in the target cell includes cytoplasm, mitochondria, proteins or biomolecules.

15. The method of claim 9,
wherein the material in the target cell includes a biomaterial selected from the group consisting of an amino acid, a nucleotide, an amino acid ester, an amino acid amide, an amino alcohol, and combinations thereof.

16. The method of claim 9,
wherein the material includes human serum albumin (HSA).

\* \* \* \* \*